(12) United States Patent
Daboush et al.

(10) Patent No.: US 10,709,744 B1
(45) Date of Patent: Jul. 14, 2020

(54) PROBIOTIC BIOFILM SUPPOSITORIES

(71) Applicant: MYBIOTICS PHARMA LTD., Ness Ziona (IL)

(72) Inventors: David Daboush, Mishmar David (IL); Stephanie Cohen, Rehovot (IL); Dorit Rozner, Gedera (IL)

(73) Assignee: MYBIOTICS PHARMA LTD., Ness Ziona (IL)

( * ) Notice: Subject to any disclaimer, the term of this patent is extended or adjusted under 35 U.S.C. 154(b) by 0 days.

(21) Appl. No.: 16/368,030

(22) Filed: Mar. 28, 2019

(51) Int. Cl.

| A61K 35/747 | (2015.01) |
|---|---|
| A61K 9/02 | (2006.01) |
| A61K 9/14 | (2006.01) |
| A61K 35/745 | (2015.01) |
| A61P 5/02 | (2006.01) |
| A61P 1/00 | (2006.01) |
| A61P 31/00 | (2006.01) |
| A61P 29/00 | (2006.01) |
| A61K 9/70 | (2006.01) |
| A61P 15/02 | (2006.01) |

(52) U.S. Cl.
CPC .............. *A61K 35/747* (2013.01); *A61K 9/02* (2013.01); *A61K 9/14* (2013.01); *A61K 9/7007* (2013.01); *A61K 35/745* (2013.01); *A61P 1/00* (2018.01); *A61P 15/02* (2018.01); *A61P 29/00* (2018.01); *A61P 31/00* (2018.01)

(58) Field of Classification Search
CPC .. A61K 35/747; A61K 9/7007; A61K 35/745; A61K 9/14; A61K 9/02; A61P 31/00; A61P 15/02
See application file for complete search history.

(56) References Cited

U.S. PATENT DOCUMENTS

| 4,250,169 | A * | 2/1981 | Hosoi | A61K 31/70 |
|---|---|---|---|---|
| | | | | 424/DIG. 15 |
| 2009/0162323 | A1 | 6/2009 | Boehm et al. | |
| 2012/0129693 | A1 | 5/2012 | Ano | |
| 2012/0237489 | A1* | 9/2012 | Heil | A61K 9/0031 |
| | | | | 424/93.44 |
| 2014/0147417 | A1 | 5/2014 | Sadiwsky et al. | |
| 2014/0363398 | A1 | 12/2014 | Jones et al. | |
| 2019/0209626 | A1 | 7/2019 | Li et al. | |
| 2019/0307817 | A1 | 10/2019 | Fichorova et al. | |

FOREIGN PATENT DOCUMENTS

| DE | 202013103204 U1 | 7/2013 | |
|---|---|---|---|
| WO | WO 2010/103374 A2 * | 9/2010 | |
| WO | 2015134808 A2 | 9/2015 | |
| WO | 2018013583 | 1/2018 | |

OTHER PUBLICATIONS

Sara E. Jones et al., "Probiotic Lactobacillus reuteri biofilms produce antimicrobial and anti-inflammatory factors", BMC Microbiology, vol. 9, pp. 35-43, 2009.
Gordon Ramage et al., "A seed and feed model for the formation of Cndida albicans biofilms under flow conditions using an inproved modified Robbins device" Revista Iberoamericana de Micologia, vol. 25, No. 1, pp. 37-40, 2008.
I. Cleenwerck et al., "Re-examination of the genus Acetobacter, with descriptions of *Acetobacter cerevisiae* sp. nov. and *Acetobacter malorum* sp. nov.", International Journal of Systematic and Evolutionary Microbiology, vol. 52, Pt. 5, pp. 1551-1558, 2002.
Ingegerd Adlerberth et al., "A Mannose-Specific Adherence Mechanism in Lactobacillus plantarum Conferring Binding to the Human Colonic Cell Line HT-29", Applied and Environmental Microbiology, vol. 62, No. 7, pp. 2244-2251, 1996.
Seung Chul Shin et al., "Drosophila Microbiome Modulates Host Developmental and Metabolic Homeostasis via nsulin Signaling", Science, vol. 334, No. 6056, pp. 670-674, 2011.
Wean Sin Cheow et al., "Controlled release of Lactobacillus rhamnosus biofilm probiotics from alginate-locust bean gum microcapsules", Carbohydrate Polymers, vol. 103, pp. 587-595, 2014.
Cheow et al., "Biofilm-Like Lactobacillus rhamnosus Probiotics Encapsulated in Alginate and Carrageenan Microcapsules Exhibiting Enhanced Thermotolerance and Freeze-Drying Resistance", Biomacromolecules 2013, 14, 3214-3222.
Liu, et al., "The essential role of hydrodynamic shear force in the formation of biofilm and granular sludge", Water Research 36 (2002) 1653-1665.
Gottschick, et al., "Screening of Compounds against Gardnerella vaginalis Biofilms", Plos One, 2016.

* cited by examiner

*Primary Examiner* — Kade Ariani
(74) *Attorney, Agent, or Firm* — The Roy Gross Law Firm, LLC; Roy Gross

(57) ABSTRACT

Compositions comprising 10% to 50% (w/w) of at least one probiotic bacteria in the form of biofilm, and lipophilic carriers are provided. Further, process for making such compositions and methods of use are provided.

14 Claims, 16 Drawing Sheets
(1 of 16 Drawing Sheet(s) Filed in Color)

PROBIOTIC BIOFILM SUPPOSITORIES

FIELD OF INVENTION

The present invention is directed to the field of probiotics delivery.

BACKGROUND OF THE INVENTION

A healthy microbiota requires bacterial colonization which provides the host multiple benefits including resistance to a broad spectrum of pathogens, essential nutrient biosynthesis and absorption, and immune stimulation that maintains a healthy gut epithelium and an appropriately controlled systemic immunity. In settings of dysbiosis or disrupted symbiosis, microbiota functions can be lost or deranged, resulting in increased susceptibility to pathogens, altered metabolic profiles, or induction of proinflammatory signals that can result in local or systemic inflammation or autoimmunity.

Urogenital infections such as yeast vaginitis, bacterial vaginosis, and urinary tract infection remain a major medical problem in terms of the number of women afflicted each year. These diseases affect the organs and tissues related to the reproductive system.

For all women up to the age of 40, microbiota is mainly represented by lactobacilli, and in pathological complications of the urogenital tract of women, the microbial composition of the biocoenosis is characterized by a decrease in the number of lactobacilli and their replacement by pathogenic anaerobic microorganisms. A change in the vaginal flora characterized by the decrease of lactobacilli appears to be the major factor causing the syndrome bacterial vaginosis.

Although antimicrobial therapy is generally effective at eradicating these infections, there is still a high incidence of recurrence. The patient's quality of life is affected and many women become frustrated by the cycle of repeated antimicrobial agents whose effectiveness is diminishing due to increasing development of microbial resistance.

Regular administration of a *Lactobacillus* strain with ability to colonize vaginal tissue can be an alternative solution for this problem. It has been shown that promising results can be obtained by using a treatment of both antibiotics and probiotics in parallel. However, it is well established in numerous studies that commercial probiotics both supplements of planktonic powders and fermented foods exert little to no health effect and lack the ability to directly deliver viable bacteria to the rectal area or the vaginal area.

There is a need for a vaginal suppositories formulation in which the probiotics are viable under the vaginal conditions, are able to adhere to the vaginal epithelial cells for a successful colonization. Moreover, it is important that such formulations are resistant to the common antibiotics used in the treatment.

SUMMARY OF THE INVENTION

According to one aspect, there is provided a composition comprising at least one probiotic bacteria in the form of biofilm and a first lipophilic carrier, wherein the at least one probiotic bacterium is 10% to 50% (w/w) of the total composition.

In some embodiments, the composition is formulated for vaginal administration, rectal administration, or both.

In some embodiments, the composition further comprises a first agent.

In some embodiments, the at least one probiotic bacteria in the form of biofilm is in the form of a powder.

In some embodiments, the at least one probiotic bacteria in the form of biofilm is homogeneously dispersed within the first lipophilic carrier and the first agent, forming a first layer.

In some embodiments, the composition further comprises a second layer.

In some embodiments, the second layer comprises a second lipophilic carrier, a second agent or both.

In some embodiments, the composition is in a form of a suppository.

In some embodiments, the first lipophilic carrier and the second lipophilic carrier are solid at room temperature and are each independently characterized by melting point of at least 25° C.

In some embodiments, the first lipophilic carrier and the second lipophilic carrier have each independently a melting point in the range of 25° C. to 60° C.

In some embodiments, the first lipophilic carrier and the second lipophilic carrier comprise one or hydrogenated fats.

In some embodiments, the second lipophilic carrier has a melting point at least 5° C. higher than the first lipophilic carrier.

In some embodiments, the first lipophilic carrier has a melting point at least 5° C. higher than the second lipophilic carrier.

In some embodiments, the release of at the least one probiotic bacteria in the form of biofilm is slower than the release of the second agent.

In some embodiments, the first lipophilic carrier and the second lipophilic carrier comprise cacao butter, palm oil, plant wax, vegetable wax, or any combination thereof.

In some embodiments, the biofilm is in a form of particles.

In some embodiments, the average diameter of the particles is in the range of 50 micrometers to 1500 micrometers (μm).

In some embodiments, the at least one probiotic bacteria is selected from the genera *Lactobacillus, Bifidobacterium, Saccharomyces, Streptococcus, Faecalibacterium*, and any combination thereof.

In some embodiments, the at least one probiotic bacteria are selected from the group consisting of *Lactobacillus crispatus, Lactobacillus gasseri, Lactobacillus iners, Lactobacillus jensenii, Lactobacillus rhamnosus, Lactobacillus Lactobacillus rhamnosus* GG, *Lactobacillus acidophilus, Lactobacillus plantarum, Lactobacillus paracasei, Lactobacillus delbrueckii* ssp. *Bulgaricus*, and any combination thereof.

In some embodiments, the first agent and the second agent is an antibiotic.

In some embodiments, any one of the first agent and the second agent is a pH adjusting agent selected from the group consisting of sodium bicarbonate, ascorbic acid, citric acid, acetic acid, fumaric acid, propionic acid, malic acid, succinic acid, gluconic acid, tartaric acid, lactic acid, boric acid and cranberry extract.

In some embodiments, the composition further comprises a stabilizer, a preservative, a lubricant, a viscosity modifying agent, a buffering agent, fatty acids, and combinations thereof.

In some embodiments, the composition is for use in treating or preventing a urogenital infection, dysbiosis, ulcerative colitis, inflammatory bowel disease (IBD), Crohn's disease, or any combination thereof in subject in need thereof.

In some embodiments, the composition is for use in treating or preventing yeast vaginitis, viral infection, fungal infection, bacterial vaginosis, urinary tract infection, or any combination thereof, in subject in need thereof.

In some embodiments, the composition is for use in modifying bacterial composition, or restoring the native vaginal flora gut flora, or both, in a target site of a subject in need thereof.

In some embodiments, the at least one probiotic bacteria in the form of biofilm is personalized for the subject.

According to another aspect, there is provided a method for treating or reducing the risk of urogenital infections, dysbiosis, ulcerative colitis, inflammatory bowel disease (IBD), Crohn's disease, or any combination thereof, in a subject, comprising administering an effective amount of the composition to the subject.

In some embodiments, the release of the at least one probiotic bacteria in the form of biofilm is controlled by the lipophilic carrier and the agent.

According to another aspect, there is provided a process for producing the composition, comprising the steps of (i) mixing at least one probiotic bacteria in the form of biofilm with a first lipophilic carrier, and optionally a first agent, thereby forming a mixture and (ii) heating the mixture to a first heating temperature.

In some embodiments, the process further comprises the step of (iii) adding a second lipophilic carrier and a second agent.

In some embodiments, the ratio of the at least one probiotic bacteria in the form of biofilm and the first lipophilic carrier, is in the range of 1:1 to 1:10.

In some embodiments, the ratio of the at least one probiotic bacteria in the form of biofilm and the first agent, is in the range of 1:0.1 to 10:1.

In some embodiments, the first lipophilic carrier and the second lipophilic carrier comprise one or more hydrogenated fats.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
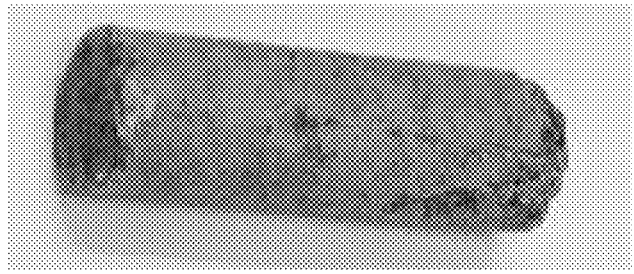
FIGS. 1A-1G present pictures of the different suppository formulations presented in table 1 (FIGS. 1A-1F), and a diagram of the experimental design and assays that were performed to optimize growth of bacteria in biofilm using bacteria in form of biofilm as well as to evaluate bacteria in form of biofilm developmental phase. The use of pH 3.5 in the pH resistance assay was determined to have a pH value close to the pH that prevails in woman vagina (pH 4-5). Susceptibility of planktonic bacteria to the resistance assays was also determined and results were subsequently compared to bacteria in form of biofilm results. CFU, colonies forming units (FIG. 1G)

According to some embodiments, the present invention provides a composition comprising at least one probiotic bacteria in the form of biofilm and a lipophilic carrier.

According to some embodiments, the present invention provides a composition comprising at least one probiotic bacteria in the form of biofilm and a first lipophilic carrier, wherein the at least one probiotic bacterium is 10% to 50% (w/w) of the total composition.

In some embodiments, the at least one probiotic bacterium is 12% to 50% (w/w), 15% to 50% (w/w), 20% to 50% (w/w), 12% to 48% (w/w), 12% to 15% (w/w), 12% to 42% (w/w), 12% to 40% (w/w), 15% to 48% (w/w), 15% to 40% (w/w), 20% to 50% (w/w), 20% to 48% (w/w), 20% to 45% (w/w), or 20% to 40% (w/w), of the total composition.

In some embodiments, the at least one probiotic bacteria in the form of biofilm is in the form of a powder.

In some embodiments, the composition is formulated for vaginal administration. In some embodiments, the composition is formulated for rectal administration. In some embodiments, the composition is formulated for vaginal administration and rectal administration.

In some embodiments, the composition further comprises a first agent.

In some embodiments, the at least one probiotic bacteria in the form of biofilm is homogeneously dispersed within the first lipophilic carrier and the first agent, forming a first layer.

In some embodiments, the composition further comprises a second layer. In some embodiments, the second layer comprises a second lipophilic carrier, a second agent or both.

In some embodiments, the composition is in a form of a suppository.

In some embodiments, the biofilm is in a form of particles.

In some embodiments, the average diameter of the particles is in the range of 50 micrometers to 1500 micrometers (µm). In some embodiments, average diameter of the particles is in the range of 50 µm to 1200 µm, 50 µm to 1100 µm, 50 µm to 1000 µm, 55 µm to 1200 µm, 55 µm to 1000 µm (µm), 57 µm to 1200 µm, or 60 µm to 1000 µm, including any range therebetween.

In some embodiments, the at least one probiotic bacteria are selected from the group consisting of *Lactobacillus crispatus*, *Lactobacillus* Gasseri, *Lactobacillus iners*, *Lactobacillus Jensenii*, *Lactobacillus rhamnosus*, and any combination thereof.

In some embodiments, the at least one probiotic bacteria are selected from the group consisting of *Lactobacillus acidophilus* DSM24735, *Lactobacillus plantarum* DSM24730, *Lactobacillus paracasei* DSM24733, *Lactobacillus delbrueckii* ssp. *bulgaricus* DSM24734.

Lipophilic Carriers

In some embodiments, the first lipophilic carrier and the second lipophilic carrier are solid at room temperature and are each independently characterized by melting point of at least 25° C. In some embodiments, the first lipophilic carrier and the second lipophilic carrier are solid at room temperature and characterized by melting point of at least 26° C., at least 27° C., at least 28° C., at least 29° C., at least 30° C., at least 31° C., or at least 32° C., including any value therebetween.

In some embodiments, the first lipophilic carrier and the second lipophilic carrier have each independently a melting point in the range of 25° C. to 60° C. In some embodiments, the first lipophilic carrier and the second lipophilic carrier have each independently a melting point in the range of 27° C. to 60° C., 30° C. to 60° C., 25° C. to 58° C., 25° C. to 55 C, 27° C. to 58° C., or 27° C. to 55° C., including any range therebetween.

In some embodiments, the first lipophilic carrier and the second lipophilic carrier comprise one or more fatty acids with a saturated content of more than 40%. In some embodiments, the first lipophilic carrier and the second lipophilic carrier comprise one or more fatty acids with a saturated content of more than 41%, more than 45%, more than 48%, or more than 50%, including any value therebetween.

In some embodiments, the first lipophilic carrier and the second lipophilic carrier comprise one or more hydrogenated fats.

As used herein the term "hydrogenated fats" refers to fatty acids that have been chemically altered. In general, hydrogenated fats are oils whose chemical structures were changed to become solid fats.

In some embodiments, the second lipophilic carrier has a melting point at least 5° C., at least 6° C., at least 7° C., at least 10° C., at least 12° C., or at least 15° C., higher than the first lipophilic carrier.

In some embodiments, the first lipophilic carrier has a melting point at least 5° C., at least 6° C., at least 7° C., at least 10° C., at least 12° C., or at least 15° C., higher than the second lipophilic carrier.

In some embodiments, the melting point of the composition is controlled by controlling the ratio of hydrogenated fats. In some embodiments, the release time of the probiotic bacteria, is controlled by the melting point of the composition. In some embodiments, the release time of the first agent, is controlled by the melting point of the composition.

In some embodiments, the release time of the second, is controlled by the melting point of the composition.

In some embodiments, the release of the at least one probiotic bacteria in the form of biofilm is slower than the release of the second agent.

In some embodiments, the first lipophilic carrier and the second lipophilic carrier comprise cacao butter, palm oil, plant wax, vegetable wax, or any combination thereof.

In some embodiments, the first lipophilic carrier and the second lipophilic carrier comprise fatty acids derived from raw materials of vegetable origin.

In some embodiments, excipients are obtained by the esterification of fatty acids with alcohols such as glycerol, polyglycerol, propylene glycol and polyethylene glycol, and by the alcoholysis of vegetable oils and fats with glycerol, polyethylene glycol and propylene glycol.

Agents

In some embodiments, the composition comprises probiotic bacteria in the form of biofilm a lipophilic carrier, and a first agent, in the form of a first layer. In some embodiments, the composition further comprises a second layer comprising a second agent.

In some embodiments, any one of the first agent and the second agent is an agent that improves the receptiveness of the vaginal tissue for colonizing probiotic bacteria. For example, an agent that may improve the receptiveness of the vaginal tissue for colonizing probiotic bacteria may be a pH modifier. In such case the lipophilic carrier is used to release an amount of a pH modifier that is sufficient to decrease the local pH in the vaginal tissue. Preferably, vaginal pH should be modified to about 4 which is optimal for colonization of the probiotic bacteria of the invention. In some embodiments, the pH modifier can be synthetic. In some embodiments the pH modifier can be natural-biological In some embodiments, any one of the first agent and the second agent is a pH adjusting agent. In some embodiments, any one of the first agent and the second agent is a pH adjusting agent capable of adjusting the pH to 4.

Non-limiting examples of pH adjusting agents according to the present invention are sodium bicarbonate, ascorbic acid, citric acid, acetic acid, fumaric acid, propionic acid, malic acid, succinic acid, gluconic acid, tartaric acid, lactic acid, boric acid and cranberry extract.

In some embodiments, any one of the first agent and the second agent is an antibiotic.

In some embodiments, the antibiotic is any antibiotic used for treatment of bacterial vaginosis. Non-limiting examples of antibiotics include metronidazole (Flagyl), clindamycin (Cleocin), and metronidazole.

In some embodiments, the antibiotic is released first. In some embodiments, the probiotic bacteria is released after release of the antibiotic.

In some embodiments, the composition further comprises a stabilizer, a preservative, a lubricant, a viscosity modifying agent, a buffering agent, fatty acids, and combinations thereof.

One of skill in the art will appreciate that the order of the carriers and agents may be altered in various embodiments and that the nomenclature "first lipophilic carrier", "first agent" and "second lipophilic carrier", "second agent" is used herein for ease of reference. For instance, in some embodiments the second agent can be selected to be mixed with the one or more lipophilic carriers and the probiotic bacteria in the form of biofilm in the first layer. One of skill in the art will further appreciate that various systems may comprise more than two lipophilic carriers or agents.

Probiotic Bacteria

In some embodiments, the biofilm particles comprise probiotic bacteria. The term "biofilm particles" refers to bacteria (e.g., probiotic bacteria) in the form of biofilm and in a form of particles.

As used herein, the term "probiotic" refers to a beneficial or required bacterial strain that can also stimulate the growth of other microorganisms, especially those with beneficial properties (such as those of the vaginal flora and gut flora).

In some embodiments, the biofilm particles comprise at least one bacterial strain derived from vaginal microflora. In some embodiments, the at least one bacterial strain derived from vaginal microflora is a probiotic bacterium.

In some embodiments, the biofilm particles comprise at least one bacterial strain derived from gut microflora. In some embodiments, the at least one bacterial strain derived from gut microflora is a probiotic bacterium.

In some embodiments, the biofilm particles comprise at least one bacterial strain derived from the colon. In some embodiments, the biofilm particles comprise at least one bacterial strain derived from the stomach. In some embodiments, the biofilm particles comprise at least one bacterial strain derived from the small intestine.

In some embodiments, the at least one probiotic bacteria is selected from the genera *Lactobacillus, Bifidobacterium, Saccharomyces, Enterococcus, Streptococcus, Faecalibacterium, Pediococcus, Leuconostoc, Bacillus, Escherichia coli*, and any combination thereof.

Non-limiting examples of gut-derived strains include *Lactobacillus rhamnosus* GG (LGG), *Streptococcus thermophiles, Lactobacillus acidophilus, Bifidobacterium lactis, Bifidobacterium breve, Bifidobacterium longum, Bifidobacterium infantis, Enterococcus faecium, Lactobacillus plantarum, Lactobacillus rhamnosus, Propionibacterium freudenreichii, Bifidobacterium breve, Lactobacillus reuteri, Lactobacillus salivarius, Bifidobacterium infantis, Streptococcus thermophiles*, and *Faecalibacterium prausnitzii*.

In some embodiments, the biofilm particles comprise at least one *Lactobacillus* bacterial strain. Non-limiting examples of *Lactobacillus* include *Lactobacillus* crispatus, *Lactobacillus* Gasseri, *Lactobacillus iners, Lactobacillus Jensenii, Lactobacillus rhamnosus, Lactobacillus Lactobacillus rhamnosus* GG, *Lactobacillus acidophilus, Lactobacillus plantarum, Lactobacillus paracasei, Lactobacillus delbrueckii* ssp. *Bulgaricus*.

In some embodiments, the probiotic bacteria can colonize a vaginal tissue. In some embodiments the probiotic bacteria are more proficient in colonizing vaginal tissue compared to similar bacteria that are provided in a planktonic form. The degree of improvement of colonization may be measured as an increase in the quantity of bacteria in samples from a tissue treated with biofilm particle-based suppositories compared to a control tissue which is treated with planktonic probiotic bacteria-based suppositories, after a predetermined period of time from administration.

In some embodiments, the bacteria provided herein is generated using the methods as disclosed in PCT/IB2016/000933 and PCT/IL2017/050587 incorporated herein by reference, in its entirety.

In one embodiment, one or more bacterium for generating biofilm particles provided herein is obtained from a healthy mammal. In one embodiment, the bacterium is obtained from an animal donor. In one embodiment, the donor may be screened for their health status and nutrition habits. In one embodiment, the bacterium is derived from a bacterial strain. In some embodiments, the bacterium is derived from stored bacterial strain. In some embodiments, the plurality of bacterium is derived from freezed bacterial strain. In some embodiments, the bacterium is derived from freezed biofilm. In some embodiments, the bacterium is derived from lyophilized bacterial strain.

In one embodiments, the biofilm particles comprise at least one bacterial strain derived from a stored microbiota sample. In one embodiment, the biofilm particles comprise at least one bacterial strain derived from a bacterial colony.

According to some embodiments, the particles in the composition described herein are adapted, configured or suitable for biofilm formation.

Use of the Composition

In some embodiments, the composition is adapted to colonize a vagina of a subject in need thereof. In some embodiments, the composition is adapted to colonize a rectum in a subject in need thereof.

In some embodiments, the composition is for use in treating or preventing a urogenital infection, dysbiosis, or both.

In some embodiments, the composition is for use in treating or preventing ulcerative colitis, inflammatory bowel disease (IBD), Crohn's disease, or any combination thereof in subject in need thereof.

In some embodiments, the composition is for use in treating or preventing yeast vaginitis, viral infection, fungal infection, bacterial vaginosis, urinary tract infection, or any combination thereof, in subject in need thereof.

In some embodiments, the composition is for use in modifying bacterial composition, or restoring the native vaginal flora, gut flora, or both, in a target site of a subject in need thereof.

In some embodiments, modifying bacterial composition in a subject refers to reduction or elimination of an unwanted bacteria, in the subject.

In some embodiments, the at least one probiotic bacteria in the form of biofilm is personalized for the subject.

In some embodiments, the composition is determined or prepared according to the profile of the subject to be treated (e.g., personalized treatment).

In some embodiments, the composition comprising one or more starins selected from *Lactobacillus plantarum, Lactobacillus paracasei, Lactobacillus acidophilus, Lactobacillus delbrueckii* sub sp. *Bulgaricus, Bifidobacterium breve, Bifidobacterium longum*, and *Faecalibacterium prausnitzii*.

In some embodiments, the composition is an anti-inflammatory composition comprising one or more starins selected from *Lactobacillus plantarum, Lactobacillus paracasei, Lactobacillus acidophilus, Lactobacillus delbrueckii* sub sp. *Bulgaricus, Bifidobacterium breve, Bifidobacterium longum*, and *Faecalibacterium prausnitzii*.

In some embodiments, the composition is formulated for vaginal administration.

In some embodiments, the composition is formulated for rectal administration.

In some embodiments, the composition is provided in a form of suppository.

In some embodiments, the composition is provided in a form of vaginal suppository, cream, tablet, capsule, ointment, gel or microcapsule.

In some embodiments, the composition can be administered for treating a medical condition associated with any disease, medical condition, or disorder as described herein throughout in a subject in need thereof.

In some embodiments, the treatment is combined with antibiotics treatment.

In some embodiments, the treatment is prophylactic, i.e., after antibiotic treatment.

In some embodiments, the vaginal tissue is pre-treated with a colonization agent prior to administration of the suppositories, wherein the pre-treatment improves the receptiveness of the vaginal tissue for colonizing probiotic bacteria.

The Method

According to some embodiments, the present invention provides a method for treating or reducing the risk of urogenital infections, dysbiosis, or both, in a subject, comprising administering an effective amount of a composition as described herein to the subject.

According to some embodiments, the present invention provides a method for treating or reducing the risk of ulcerative colitis, inflammatory bowel disease (IBD), Crohn's disease, or any combination thereof, in a subject, comprising administering an effective amount of a composition as described herein to the subject.

In some embodiments, the release of the at least one probiotic bacteria in the form of biofilm is controlled by the lipophilic carrier and the agent.

In some embodiments, the release of the at least one probiotic bacteria in the form of biofilm is controlled by the melting temperature of the lipophilic carrier. In some embodiments, different mixtures of lipophilic carriers can be used in order to tune the melting temperature of the composition.

The Process

According to some embodiments, the present invention provides a process for producing a composition as described herein.

In some embodiments, the present invention provides a process for producing a composition as described herein, comprising the steps of (i) mixing at least one probiotic bacteria in the form of biofilm with a first lipophilic carrier, and optionally a first agent, thereby forming a mixture and (ii) heating the mixture to a first heating temperature.

In some embodiments, the process further comprises the step of (iii) adding a second lipophilic carrier and a second agent.

In some embodiments, the ratio of the at least one probiotic bacteria in the form of biofilm and the first lipophilic carrier, is in the range of 1:1 to 1:10, 1:2 to 1:10, 1:5 to 1:10, 1:1 to 1:9, 1:1 to 1:5, including any range therebetween.

The process of any one of claims 28 to 30, wherein the ratio of the at least one probiotic bacteria in the form of biofilm and the first agent, is in the range of 1:0.1 to 10:1, 1:0.5 to 10:1, 1:1 to 10:1, 1:2 to 10:1, 1:0.1 to 9:1, 1:0.1 to 8:1, 1:0.1 to 1:1, 1:0.1 to 2:1, including any range therebetween.

In some embodiments, the first lipophilic carrier and the second lipophilic carrier comprise one or more fatty acids with a saturated content of more than 40%, more than 41%, more than 45%, more than 48%, or more than 50%, including any value therebetween.

In some embodiments, the first lipophilic carrier and the second lipophilic carrier comprise one or more hydrogenated fats.

In some embodiments, the heating temperature is determined according to the melting temperature of the one or more hydrogenated fats.

General

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Strains and Culture Conditions

All strains used in this study were purchase from either ATCC or DSMZ. Strains used in this study were: *Lactobacillus* crispatus (DSM 20584), *Lactobacillus jensenii* (DSM 20557), *Lactobacillus* gasseri (DSM) and *Lactobacillus rhamnosus* (DSM/ATCC). *L. gasseri* and *L. rhamnosus* were aerobically grown in Animal-based medium (Himedia) or a Nonanimal-based growth medium suited for industrial production (NuCel by Procelys, France). *L. jensengfii* and *L. crispatus* were grown anaerobically (90% N2, 5% CO2, 5% Hz atmosphere). Anaerobic experiments were performed in the Bactron anaerobic workstation.

Planktonic Cultures

Prior to the bacteria in form of biofilm resistance assays, planktonic bacteria resistant to acidity and antibiotics were determined. For low pH assay, an overnight culture of vaginal bacteria was diluted to achieve $10^5$-$10^9$ colony forming units (CFU) per mL, based on the number of bacteria in biofilm of the specific strain. Planktonic bacteria were exposed to different acidity for 1 h at 37° C., similar to the procedure done for bacteria in form of biofilm. At the end of incubation, samples were centrifuges (max. speed, 2 min) and supernatant was removed. Bacteria pellet was then resuspended in phosphate buffered saline (PBS)×1 before plating and CFU counting.

For antibiotic assay, and overnight culture was diluted to an optical start density (OD) of 0.13. 100 μl of the culture was spread homogenously into agar plate and left for 15 min to dry prior to applying the antibiotic MIC strips (Himedia). Plates were incubated at 37° C. for 24 h before minimum inhibitory concentration (MIC) value were determined.

Bacteria in Form of Biofilm Cultures

Single Strain (Monoculture)

A culture of *Lactobacillus* sp. was started from glycerol stock (12.5%) and was incubated overnight at 37° C., 180-150 rpm at aerobically or anaerobically conditions, based on the specific strain. The culture was diluted to an OD600 of 0.05, for the final biofilm culture. The bacteria in form of biofilm cultures were obtained as described in WO2016181228A2, incorporated herein by reference in its entirety.

Bacteria in form of biofilm were grown at 37° C. with continuous stirring. All bacteria in form of biofilm experiments were carried out in laboratory-scale production either small-scale (volume of 30 mL) or medium-scale (volume of 250 mL or 500 mL in a fermenter of 2 L). Analysis of bacteria in form of biofilm growth was carried out every 24 h incubation during a total of 72 h. Each day, medium was replaced with a fresh medium and the number of bacteria in biofilm was quantified. Measurements of viable cells were done by counting CFU on agar plates. Additionally, bacteria in form of biofilm developmental stage was tested by exposing the bacteria in form of biofilm to extreme conditions such as low pH and antibiotics (for further details see section 'pH and antibiotics resistance assays'). Results were latter compared to planktonic bacteria to demonstrate the advantage of bacteria in form of biofilm over free-living bacteria.

Few experiments were conducted to obtain the best conditions for bacteria in form of biofilm growth (following the methods described above):

Agitation—bacteria in form of biofilm growth and development (resistance to pH) was compared between static (no agitation) and continuous stirring conditions (70-80 rpm) or between two agitation speeds 70-80 rpm and 130 rpm (based on the experiment).

Incubation time—bacteria in form of biofilm growth and development (resistance to pH) was investigated each 24 h for a period of 72 h.

Particle sizes—bacteria in form of biofilm growth on different particles ranging between 80-1000 μM in size, was examined: Microcrystalline cellulose (MCC) (80-150 μM), Microcrystalline cellulose: Di calcium phosphate (MCC: DCP) (1:1, ~100 μM), Cranberries (500-600 μM), Alginate (1000 μM). Bacteria in form of biofilm was grown during 24 h and assessed for their growth development.

Matrix:Medium ratio—bacteria in form of biofilm growth during 24 h was evaluated as a function of ratio between matrix (MCC) to medium. The following ratio of matrix to medium were compared: matrix was either 2%, 5%, 10% or 20% from medium.

Agitation vs. no agitation after the addition of planktonic bacteria—the effect of mixing on the attachment of planktonic bacteria to the matrix, and subsequently bacteria in form of biofilm growth, was examined. Two conditions were compared following the addition of planktonic bacteria at the beginning of experiment: continuous agitation during the all experiment (24 h incubation) vs. no-agitation at the first 2 h (apart of two times 10 sec of gentle mixing during this time) and thereafter continuous agitation till the end of the experiment.

pH and Antibiotics Resistance Assays

A sample from the media-matrix solution were transfer to tubes and then centrifuge at 500 rpm for 3 min at RT. Subsequently, the supernatant was discarded, and the pellet was washed with PBS to remove of planktonic bacteria that precipitated during centrifugation. Samples were centrifuge again at 500 rpm for 3 min at RT. Following centrifugation, supernatant was removed and for each treatment (pH or antibiotics) 1 g of bacteria in form of biofilm was used. For the pH resistance assay, bacteria in form of biofilm were exposed for 1 h to 5 mL PBS with different acidity: pH 2 and 3.5 (the pH of PBS×1 was adjusted to 2 and 3.5, respectively, using 2M HCl) for 1 h at 37° C., 100 rpm. Bacteria in form of biofilm incubated in 5 mL PBS 7 (ambient pH), with the same conditions, were applied as a control. For antibiotics assay, 1 gr of bacteria in form of biofilm were exposed to 3 sequential concentration of antibiotics, which were well above the MIC value of the specific strain. Bacteria in form of biofilm were incubated in 5 mL growth medium with or without antibiotic (the latter was used as a control) for 24 h at 37° C.

At the end of incubation, bacteria in form of biofilm were washed with 10 mL PBS×1. Following centrifugation (500 rpm, 3 min), 9 mL was removed and the bacteria in form of biofilm in the 1 mL remaining PBS solution were vortex for 1.5 min at high speed to release bacteria from biofilm that were attached to particles.

Analytical Methods

CFU were determined at the end of each resistance assay. First, serial dilutions were conducted, and bacteria were plated in triplicate onto MRS agar plates. The plates were incubated at 37° C. in aerobic or anaerobic conditions, based on the strain growth condition (see above), for 48-72 h prior to CFU counting.

Example 1

Suppositories Formulation

The formulation of the suppositories consists of bacteria in form of biofilm grown as described above, mixed in pharmaceutically acceptable excipients (oil-based carriers) and/or a prebiotic agent (such as, cranberries, ascorbic acid and antibiotics). Bacteria in form of biofilm used was either lyophilized (dry) or wet bacteria in form of biofilm. In the suppository formulation, vegetable (palm) butter and cocoa butter, in a ratio of 1:5, respectively, were melted in a hot bath at 50-52° C.

Temperature was monitored closely to not reach over a temperature that will compromise the butters (over 60° C.). Two to three drops of Lecithin were then added to the molten butters to aid with the homogeneity of the mixture. The mixture was left to cool down to 25° C. before bacteria in form of biofilm (dry) and/or prebiotic substance (such as cranberries, ascorbic acids etc.) were added in different rations of bacteria to wax. (Bacteria in form of biofilm and prebiotic) to butters, respectively. This final composition was reheated to 30° C. and was poured into vaginal suppositories molds. The suppositories were stored at 4° C. till use. To mimic the dissolution of the suppository, the suppositories were put at 37° C. in an incubator. Results are summarized in table 1 and FIGS. 1A-F.

TABLE 1

Figure 1B:
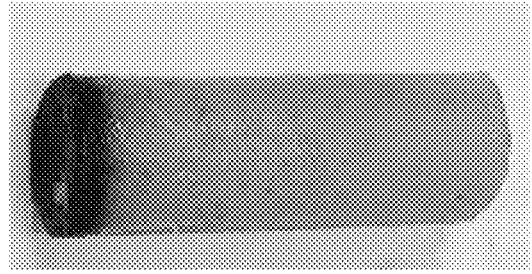
Figure 1C:
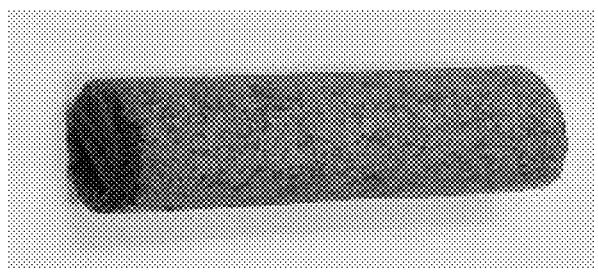
Figure 1D:
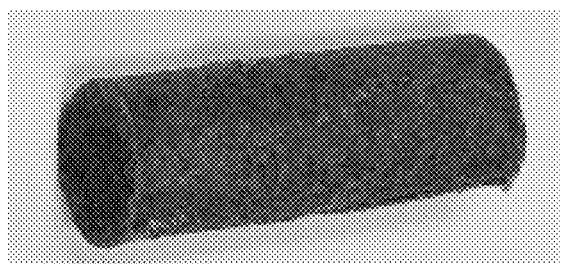
Figure 1E:
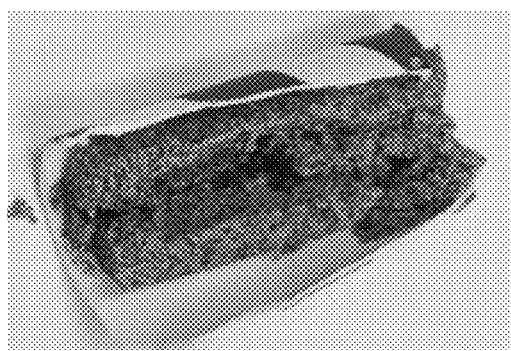

| Suppositories formulation: | Oil | MCC | Cranberries | Illustration | Melting time | % active in sup pository |
|---|---|---|---|---|---|---|
| 2 | Kahlwax 6240 4 g | 700 mg | 300 mg | FIG. 1A | 130 min | 20% |
| 3 | cocoa butter 3.8 g palm butter 0.95 g | 0.15 g | 0.1 g | FIG. 1B | 15 min | 5% |
| 4 | cocoa butter 4 g palm butter 1 g | 700 mg | 300 mg | FIG. 1C | 20 min | 20% |
| 5 | cocoa butter 2.4 g palm butter 0.6 g | 1.4 g | 600 mg | FIG. 1D | 40 min | 32% |
| 6 | cocoa butter 1.6 g palm butter 0.4 g | 2.1 g | 900 mg | FIG. 1E | disintigrate | 60% |

TABLE 1-continued

Figure 1F:
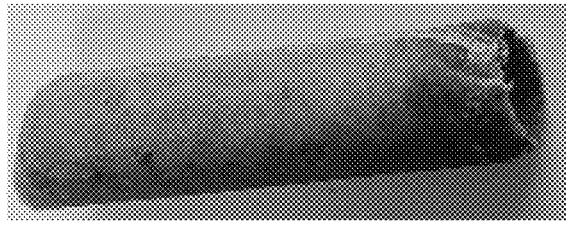

| Suppositories formulation: | Oil | MCC | Cranberries | Illustration | Melting time | % active in sup pository |
|---|---|---|---|---|---|---|
| 7 | Kahlwax 6240 2 g cocoa butter 1.15 g palm butter 0.85 g | 700 mg | 300 mg | FIG. 1F | 30 min | 20% |

Example 2

Bacteria Growth Optimization

Figure 1G:
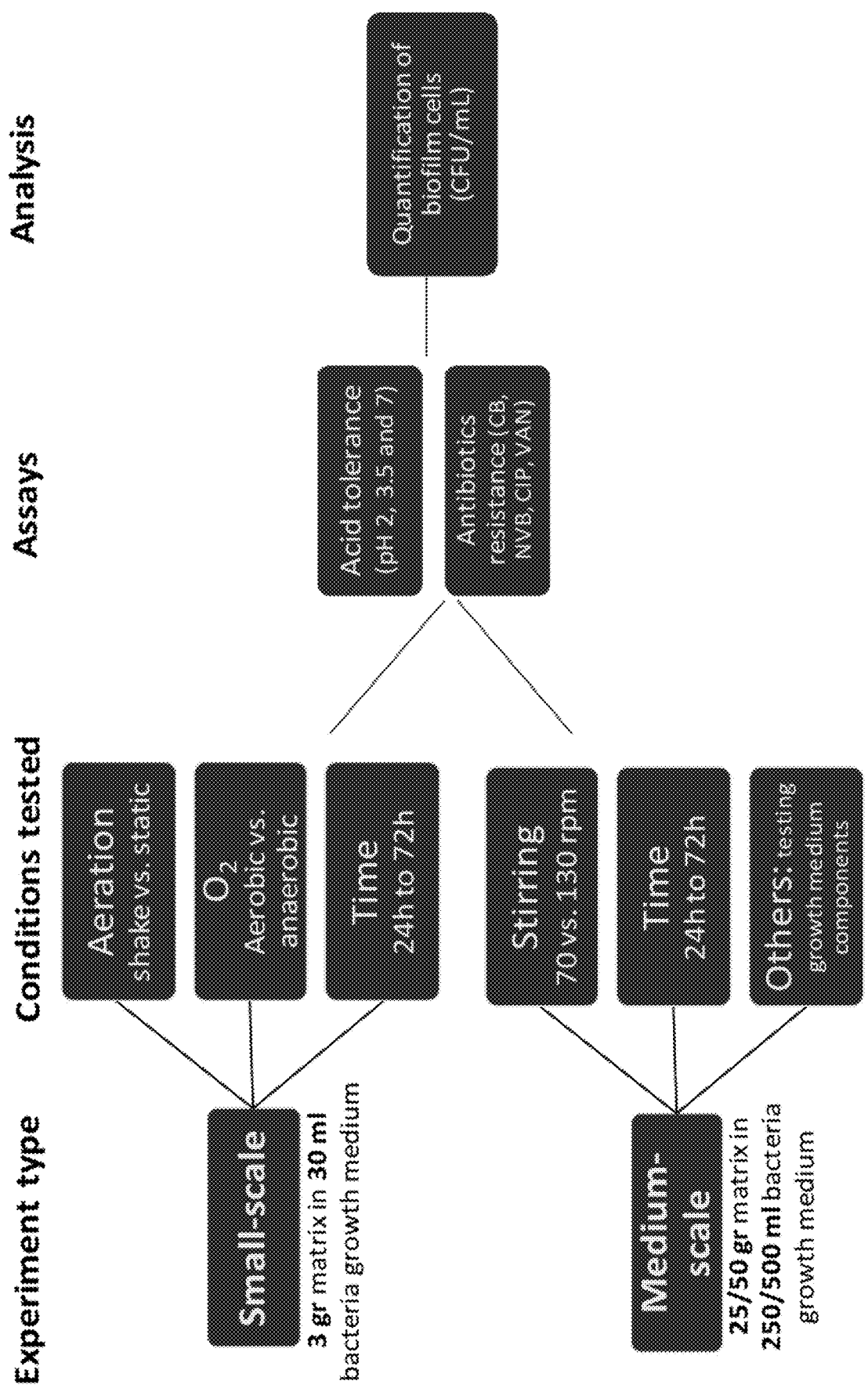

Experimental Procedure:

The application of bacteria in form of biofilm was tested with two types of experimental designs a small-scale followed by a medium-scale experiment (FIG. 1G). Based on the results obtained from the small-scale experiment, the inventors define the conditions for the medium-scale experiment. The procedure in brief: Bacteria in form of biofilm growth and developmental state was examined every 24 h incubation during a total of 72 h. Each day, medium was replaced with a fresh medium and the number of bacteria in biofilm was quantified (hereafter pH 7 treatment). Additionally, the formation and development of biofilm on the particles was tested by exposing the Bacteria in form of biofilm to extreme conditions such as acidic pH (pH 3.5 and 2) and antibiotics (CB, carbenicillin; CIP, ciprofloxacin; VAN, vancomycin; NVB, novobiocin). pH resistance assay was conducted daily, and antibiotic assay was performed following 48 h or 72 h of incubation. Results from these assays were latter compared to planktonic bacteria of the same species to show the advantage of Bacteria in form of biofilm over free-living bacteria.

| Bacteria strains selected | | |
|---|---|---|
| Strain | Type | Strain number |
| Lactobacillus jensenii | Anaerobic | DSM 20557 |
| Lactobacillus crispatus | Anaerobic | DSM 20584 |
| Lactobacillus iners | Aerobic | DSM 13335 |
| Lactobacillus gasseri | Aerobic | ATCC 33323 |
| Lactobacillus rhamnosus | Aerobic | |

For each bacteria strain tested, the results are presented as follows:

Planktonic growth;
Optimization of Bacteria in form of biofilm growth in a Small-scale set-up;
Optimization of Bacteria in form of biofilm growth in a Medium-scale set-up.

In the description of the results, a change of 1 log in bacteria yield is considered to be in the range of technical error of bacteria plating and CFU counting and thus is accounted for non-significant difference.

Figure 2:
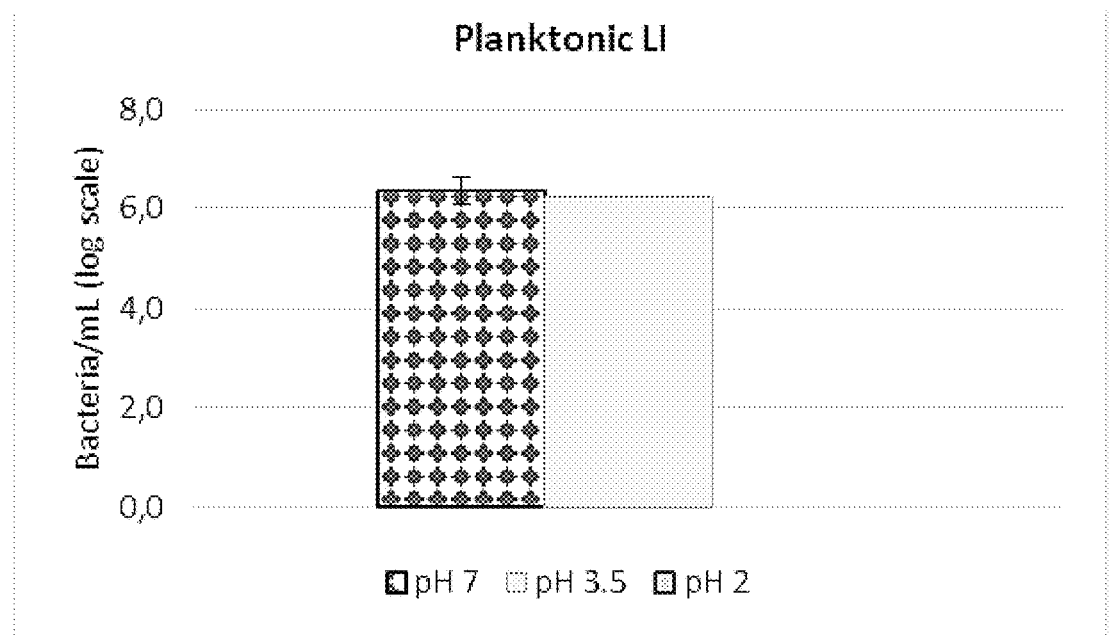
FIG. 2 presents a bar graph of acid resistance of planktonic bacteria of *L. iners*.

Planktonic bacteria produced moderate bacteria yield of ~$10^6$ cells/mL at pH 7 (control, FIG. 2). Bacteria yield at pH 3.5 was comparable to control. However, at higher acidic conditions (pH 2) planktonic bacteria did not survived.

Finally, exposure to antibiotics showed a MIC of 64 μg/mL of CB and 16 μg/mL of NVB and 4 μg/mL to VAN (Table 2).

TABLE 2

| MIC of different antibiotics for planktonic LI. Values are expressed in μg/mL | | | |
|---|---|---|---|
| Bacteria\ABX | CB | NVB | VAN |
| Lactobacillus iners | 64 | 16 | 4 |

*Lactobacillus iners* (LI) Bacteria in Form of Biofilm—Small-Scale Experiment

Figure 3:
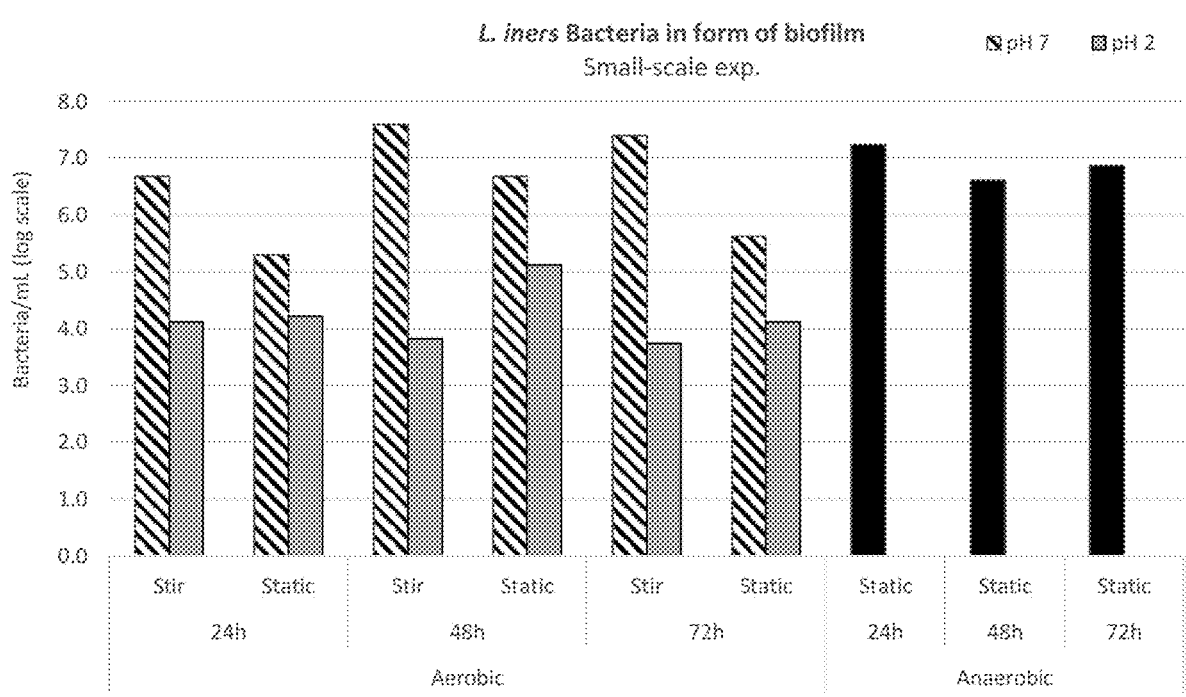
FIG. 3 presents a bar graph of acid resistance of *L. iners* Bacteria in form of biofilm following growth in a small-scale set-up. Aerobic and anaerobic conditions were examined as well as aeration condition (static vs. stir)

Results from the small-scale experiment showed the highest bacteria yield was after 48 h incubation with the matrix, in aerobic conditions with a gentle agitation (100 rpm). In contrast to planktonic bacteria, Bacteria in form of biofilm survived pH 2, with a drop of 1 to 3.8 log in bacteria growth in biofilm for agitated and non-agitated conditions, respectively (FIG. 3). However, in anaerobic conditions bacteria in biofilm did not show any advantage at low pH compared to planktonic bacteria.

LI Bacteria in Form of Biofilm—Medium-Scale Experiment

Figure 4:
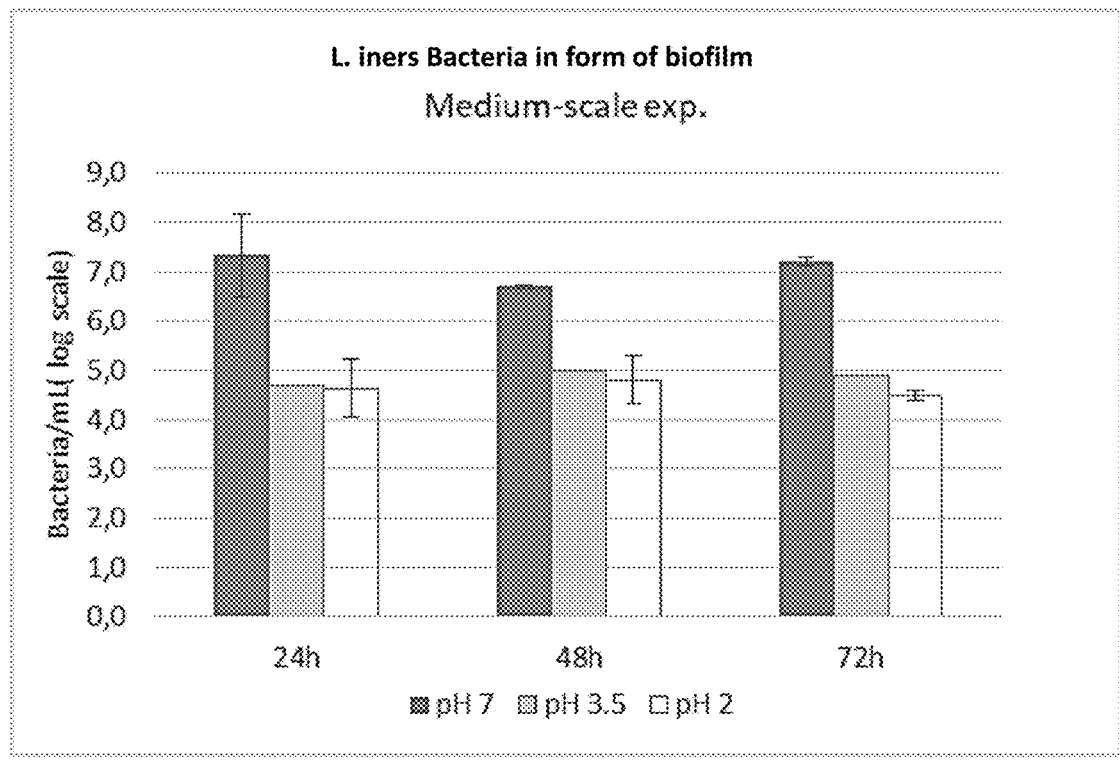
FIG. 4 presents a bar graph of acid resistance of *L. iners* Bacteria in form of biofilm following growth in a medium-scale set-up.

Based on results from the small-scale experiment, conditions employed for the growth of LI in biofilm were aerobic with a gentle agitation. Here, bacteria yield seems to be slightly higher after 24 h and 72 h incubation with the matrix compared to 48 h. Bacteria in form of biofilm survived at both acidic pH treatments and there were no significant differences in survival rate between treatments (FIG. 4).

Figure 5:
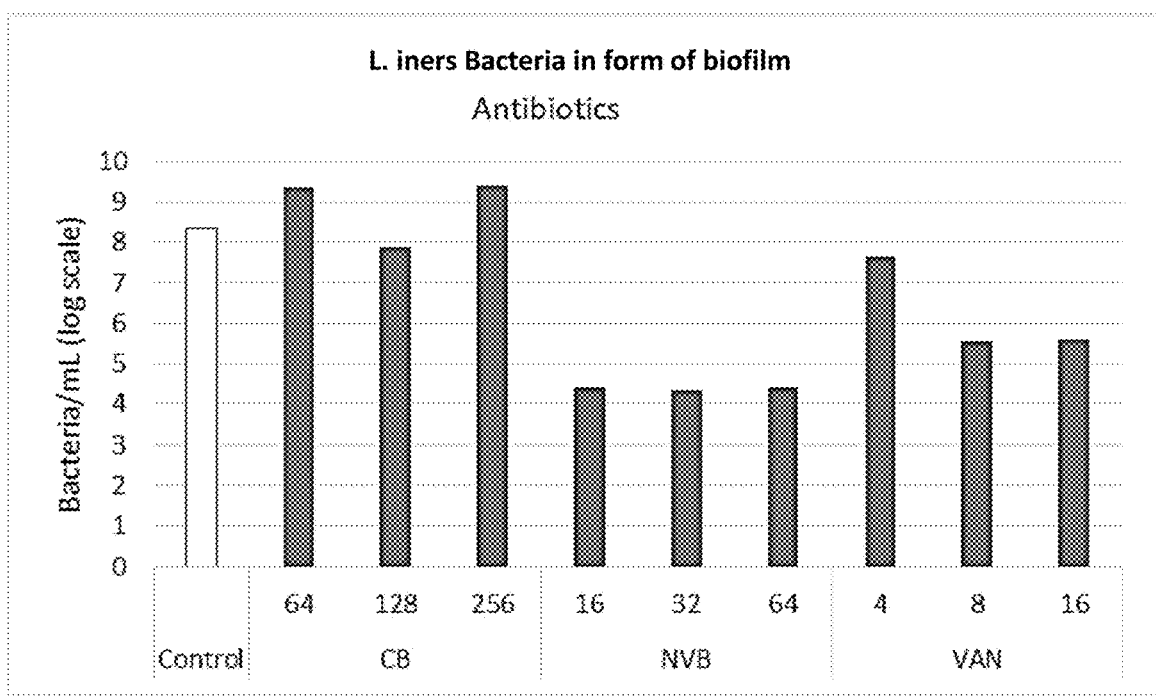
FIG. 5 presents a bar graph of antibiotics resistance of *L. iners* Bacteria in form of biofilm following growth in a medium-scale set-up. 'Control' refers to Bacteria in form of biofilm that was not exposed to antibiotics. Numbers in the x-axis are antibiotics concertation in μg/mL.

Finally, Bacteria in form of biofilm was tested for resistance to antibiotics (FIG. 5). While Bacteria in form of biofilm demonstrated resistance to all three types of antibiotics compare to planktonic bacteria, the highest resistance was observed for the CB antibiotic. When exposed to CB, bacteria yield was either not affected or slightly affected by antibiotic concentration, even after 24 h incubation. Bacteria in form of biofilm exposure to VAN and NVB antibiotics showed a similar trend of bacteria growth between incubation days: after an initial decrease of ~4 log, numbers of bacteria did not change significantly with increasing concentrations. When antibiotics resistance data are pooled together, it appears that after 48 h we obtained the highest resistance of biofilm to increasing amount of antibiotics.

In conclusion, max bacteria yield in biofilm of *L. iners*, based on the applied experimental conditions, was 107-108. LI Bacteria in form of biofilm were able to survive and/or grow well in the presence of both acidic pH and antibiotics thus demonstrating that Bacteria in form of biofilm performance was superior to that of free-living bacteria.

*L. jensenii* (LI)

Planktonic LJ

Figure 6:
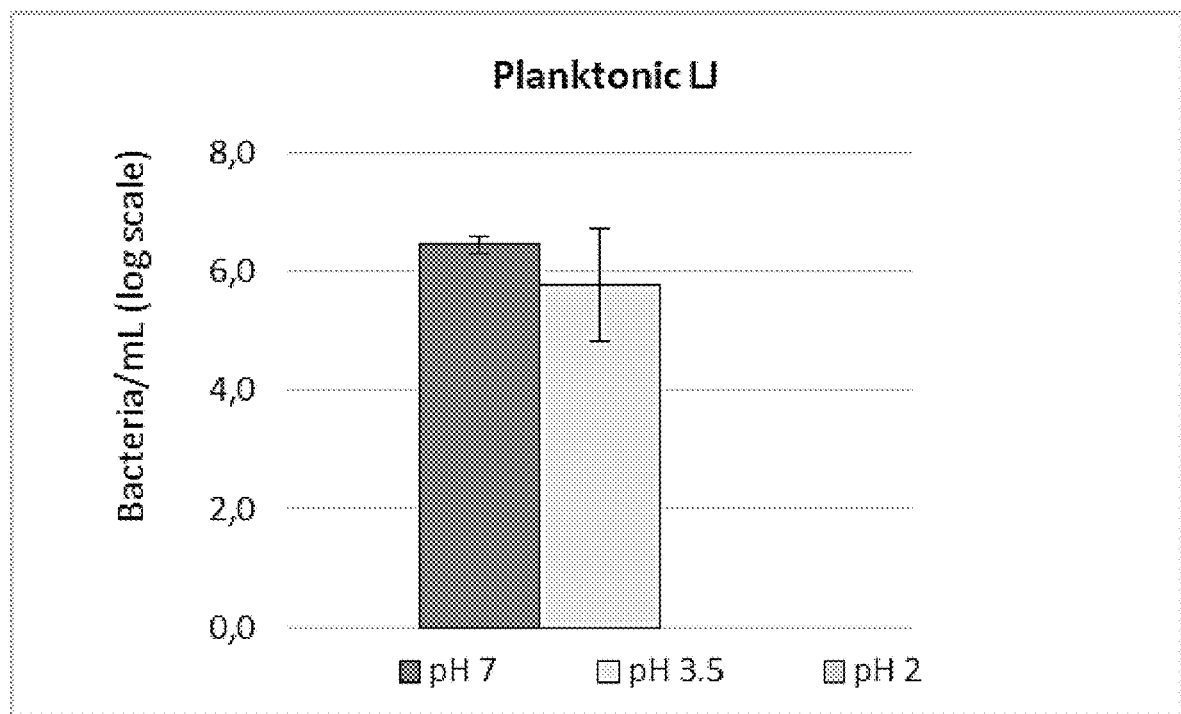
FIG. 6 presents a bar graph of acid resistance of planktonic bacteria of *L. jensenii*.

Planktonic bacteria produced bacteria yield of ~$10^6$ cells/mL at control conditions (pH 7, FIG. 6). No significant difference was observed in bacteria yield at pH 3.5 compared to control. However, planktonic bacteria did not survive exposure to pH 2.

Exposure of planktonic bacteria to CB and NVB and VAN antibiotics resulted in low bacterial resistance to antibiotic with a MIC of 8 μg/mL, 2 μg/mL and 1.5 μg/mL, respectively. However, planktonic bacteria were not susceptible to CIP and displayed full growth of bacteria cells regardless the employed antibiotic concertation (Table 4).

TABLE 4

MIC of different antibiotics for planktonic LJ Values are expressed in µg/mL

| Bacteria\ABX | CB | NVB | VAN | CIP |
|---|---|---|---|---|
| *Lactobacillus jensenii* | 8 | 2 | 1.5 | >256 |

LJ Bacteria in Form of Biofilm—Small-Scale Experiment

Figure 7:
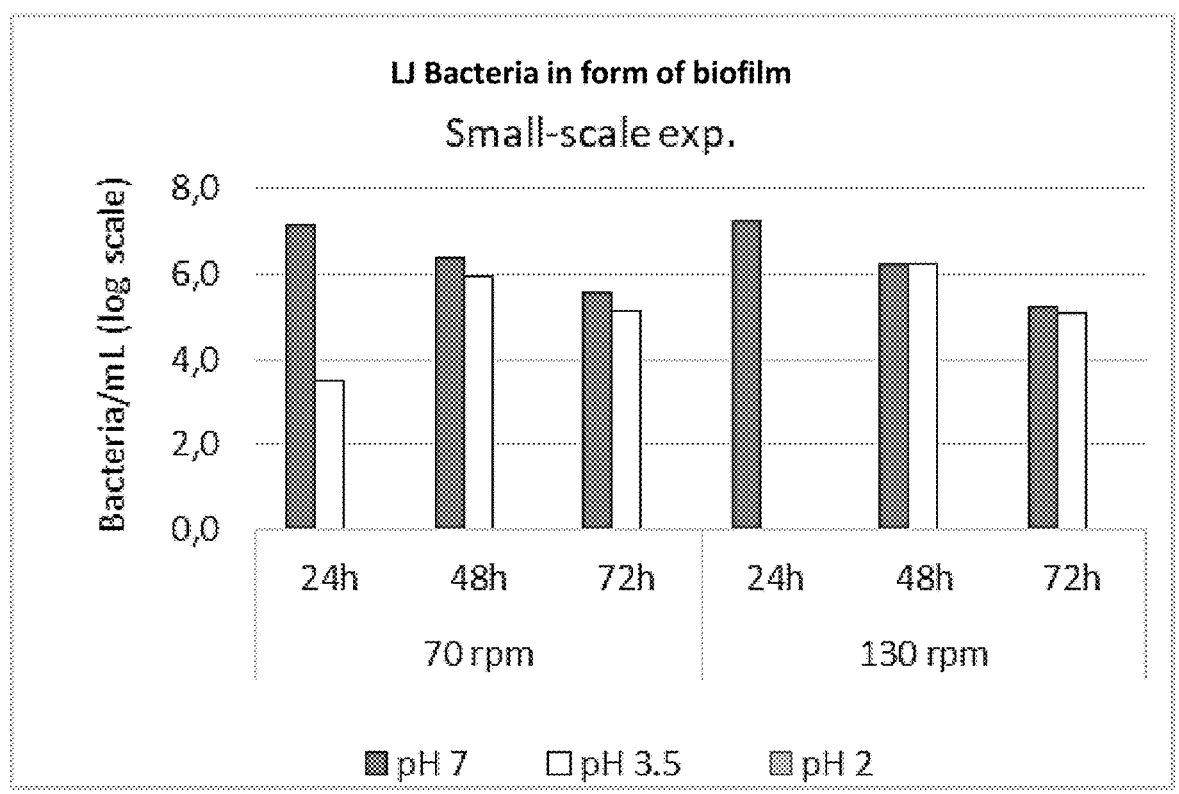
FIG. 7 presents a bar graph of acid resistance of *L. iners* Bacteria in form of biofilm following growth in a small-scale set-up while examining two agitation speeds (70 and 130 rpm)

Growth of LJ Bacteria in form of biofilm in the small-scale experimental set-up was similar at both agitation conditions (70 rpm and 130 rpm) (FIG. 7). There was a decrease over time in Bacteria in form of biofilm growth. Maximum bacteria yield of $10^7$ cells/mL was observed after 24 h of incubation while at the third day of incubation, the lowest bacteria yield ($\sim 10^5$ cells/mL) was recorded. When Bacteria in form of biofilm were exposed to pH 3.5, excluding the Pt day of incubation, there was no significant difference in bacteria number compare to control (pH 7). However, Bacteria in form of biofilm did not survive the lowest pH treatment (pH 2). In general, growth of bacteria in biofilm did not differ significantly from their free-living form. It should be noted that an experiment was performed to test whether no agitation can result in better yield of Bacteria in form of biofilm (RD206). Results showed a decrease of ~1 log in bacteria growth compare to both agitation conditions.

In the following medium-scale experiments, both agitation conditions were tested as there was no definitive conclusion regarding which stirring condition have the best effect on Bacteria in form of biofilm growth. Furthermore, as the setup of medium-scale experiments resemble better the growth conditions utilize in the industry, it was decided to examine these two agitation speeds with this type of setup as well.

LJ Bacteria in Form of Biofilm—Medium-Scale Experiment

Figure 8:
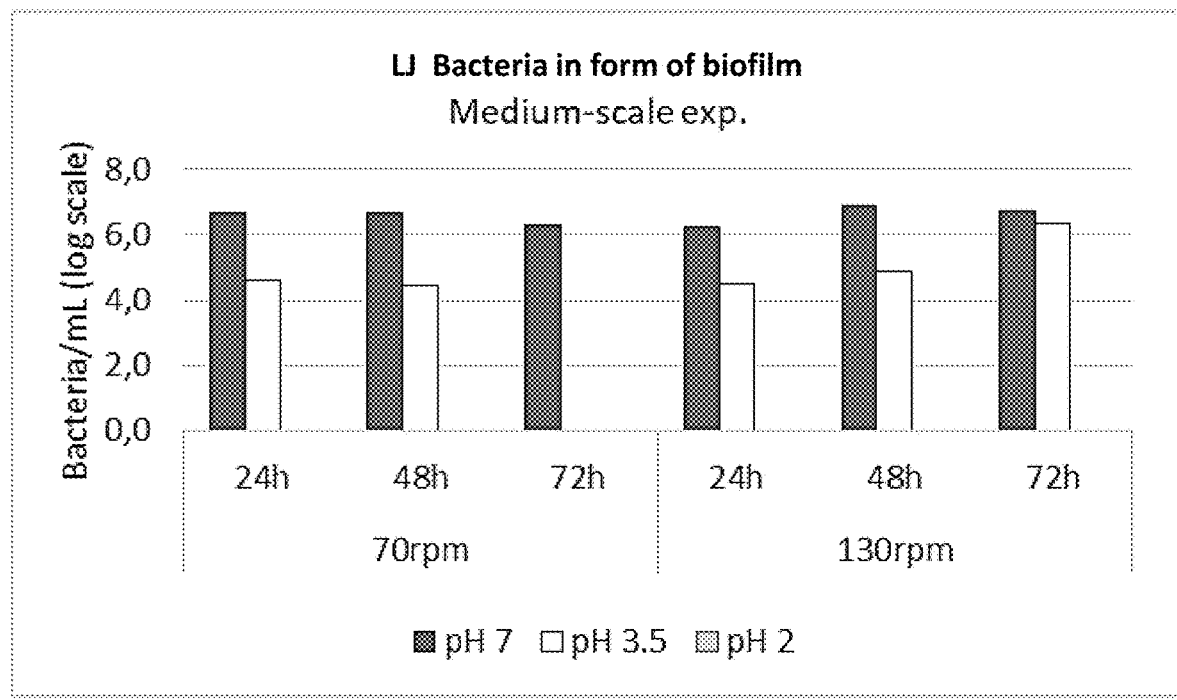
FIG. 8 presents a bar graph of acid resistance of *L. jensenii* Bacteria in form of biofilm following growth in a medium-scale set-up while examining two agitation speeds (70 and 130 rpm)

Similar to the small-scale experiment, bacteria yield in biofilm reached a maximum growth of ~$10^7$ CFU/mL, however, growth stayed stable during all 3 days of incubation (FIG. 8). Moreover, no significant difference was observed between the two agitation speeds.

Different from the former experiment, a larger decrease was observed in CFU counts after exposure to pH 3.5 (2-2.3 log at the end of the first two days of incubation (FIG. 8). When Bacteria in form of biofilm resistance to pH 2 was tested, biofilm completely disintegrated (FIG. 8). We speculate that the disappearing of cells after incubation at pH 3.5 at the 3rd day of incubation, was due to technical error. Indeed, in the following experiments, results at 72 h did not differ from the first two days of incubation.

Figure 9:
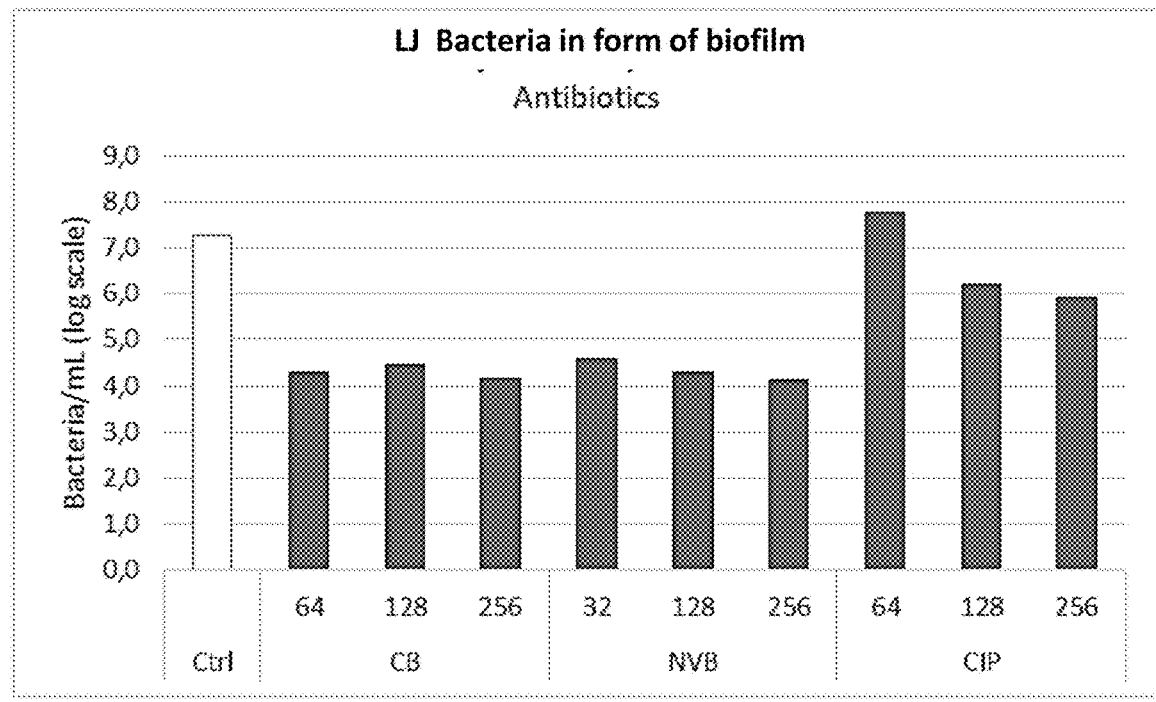
FIG. 9 presents a bar graph of antibiotics resistance of *L. iners* Bacteria in form of biofilm following growth in a medium-scale set-up. 'Ctrl' refers to Bacteria in form of biofilm that was not exposed to antibiotics. Numbers in the x-axis are antibiotics concertation in μg/mL.

Next, LJ Bacteria in form of biofilm was exposed to increase antibiotics concentrations (FIG. 9). Bacteria in form of biofilm exhibited high resistance to antibiotics compared to planktonic cells whereas the applied concentrations were well-above the MIC value for planktonic bacteria. For both NVB and CB, although after 24 h there was an initial reduction in bacteria growth, yield stayed stable regardless the antibiotic concentration.

In summary, despite Bacteria in form of biofilm results to acidic conditions, LJ Bacteria in form of biofilm demonstrated a clear advantage over planktonic bacteria when was exposed to antibiotics.

Although in the current experiment there was no difference in agitation conditions, experiments that were conducted latter, in medium-scale set-up, produced better results for Bacteria in form of biofilm growth at low agitation. Therefore, agitation for LJ Bacteria in form of biofilm in this type of experiments was set to continuous 70-80 rpm. Additionally, a preliminary experiment showed an advantage for Bacteria in form of biofilm growth when at the first day, after the addition of planktonic bacteria to the fermenter with the matrix, fermenter is kept in static conditions, for 2 h at 37 C (with a gentle mixing after 1 h). This step may allow the bacteria to better attach to the matrix and was employed in all subsequent experiments, regardless the bacteria strains that is being used.

*L. crispatus* (LCr)

Planktonic LCr

Figure 10:
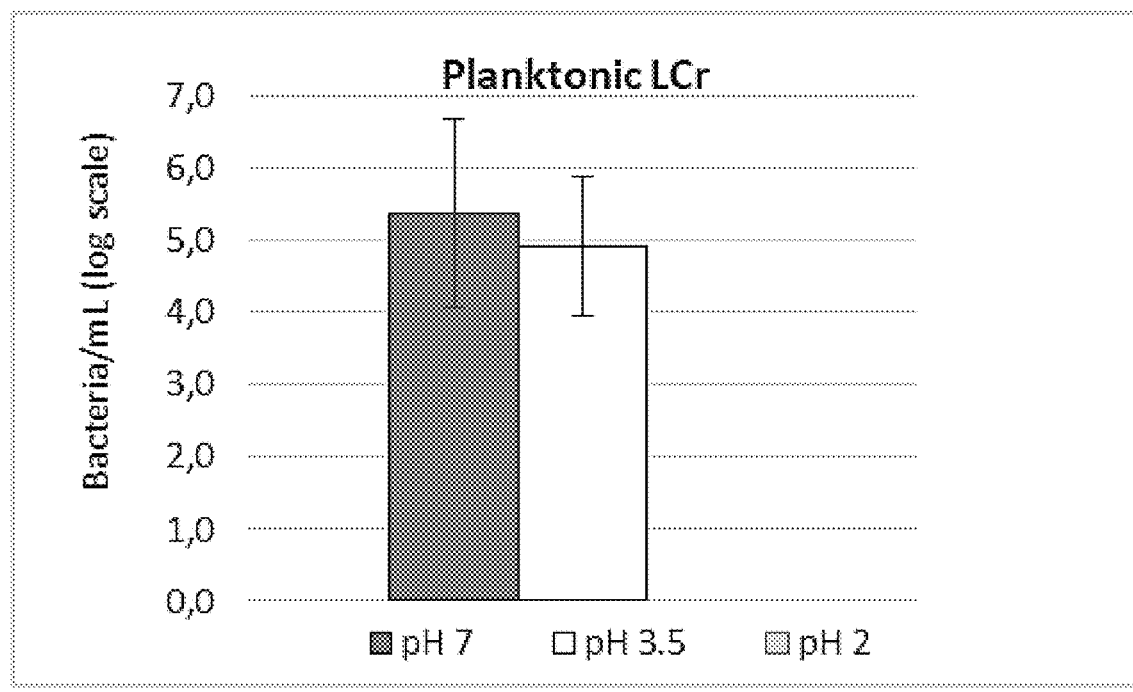
FIG. 10 presents a bar graph of acid resistance of planktonic bacteria of *L. crispatus*.

Planktonic LCr exhibited similar results to planktonic LJ when exposed to low pH treatments and increased antibiotic concentrations (FIG. 10). Exposure to pH 3.5 did not significantly affected bacteria cells compare to control (pH 7) whereas at pH 2 bacteria did not survive.

When planktonic LCr were treated with antibiotics, low bacteria resistance was observed for CB, NVB and VAN with MIC values of 4 µg/mL, 2 µg/mL and 1.5 µg/mL, respectively (Table 5). However, planktonic bacteria were not susceptible to CIP and displayed full growth of bacteria cells regardless the employed antibiotic concertation.

TABLE 5

MIC of different antibiotics for planktonic LCr Values are expressed in µg/mL.

| Bacteria\ABX | CB | NVB | VAN | CIP |
|---|---|---|---|---|
| *Lactobacillus crispatus* | 4 | 2 | 1.5 | >256 |

LCr Bacteria in Form of Biofilm—Small-Scale Experiment

Figure 11:
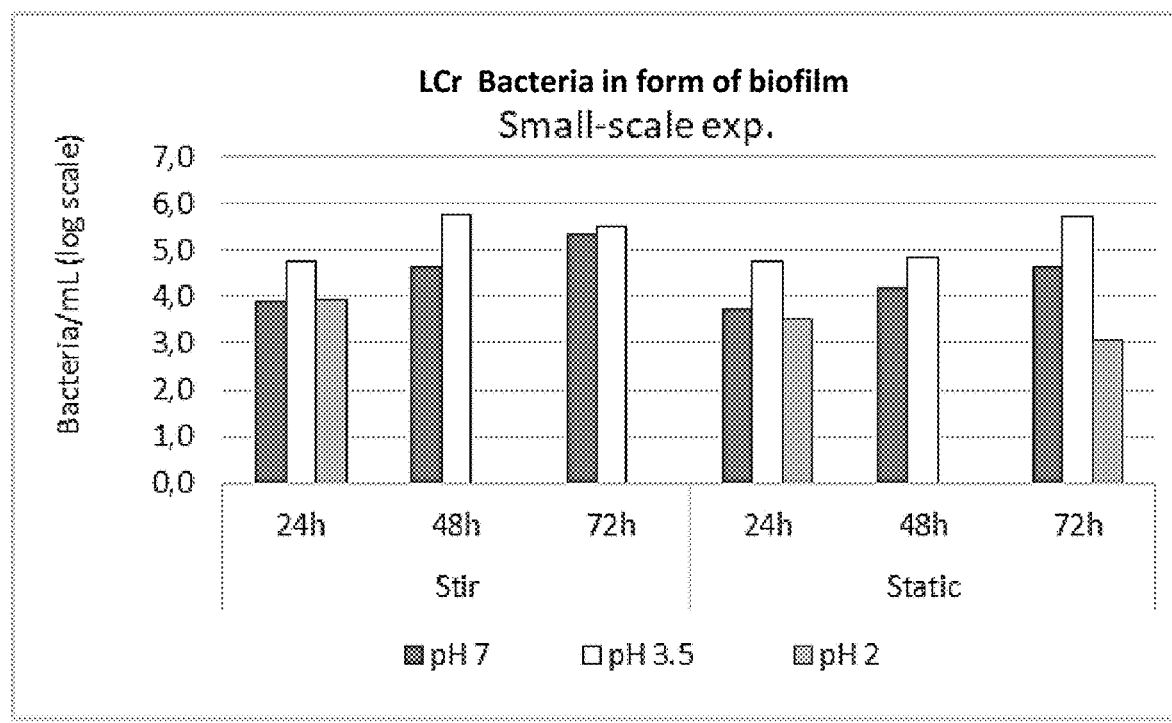
FIG. 11 presents a bar graph of acid resistance of *L. crispatus* Bacteria in form of biofilm following growth in a small-scale set-up while examining agitation and nonagitation conditions.

Whether LCr Bacteria in form of biofilm were regularly agitated or not agitated, small-scale experiment with LCr produced maximum bacteria yield of $5*10^5$ cells/mL and lowest of ~$10^4$ cells/mL (FIG. 11). In both treatments, Bacteria in form of biofilm growth was the highest after 3 days on incubation with the matrix. Surprisingly, under moderate acidic conditions (pH 3.5), an increase of ~1-2 log in bacteria yield was observed regardless the treatment. Nonetheless, at pH 2 number of bacteria in biofilm either decreased by 2-4 log or completely diminished. No pattern could be determined in their survival at this acidic condition and their resistance to pH 2 will be re-examined in the following medium-scale experiment.

Despite the similarity in the results from both stirring conditions, Bacteria in form of biofilm growth when agitated appear to produce a slightly better growth and survival at pH 7 and 3.5, respectively. Gentle agitation (70-80 rpm) was therefore employed in the next experiments.

LCr Bacteria in Form of Biofilm—Medium-Scale Experiment

Figure 12:
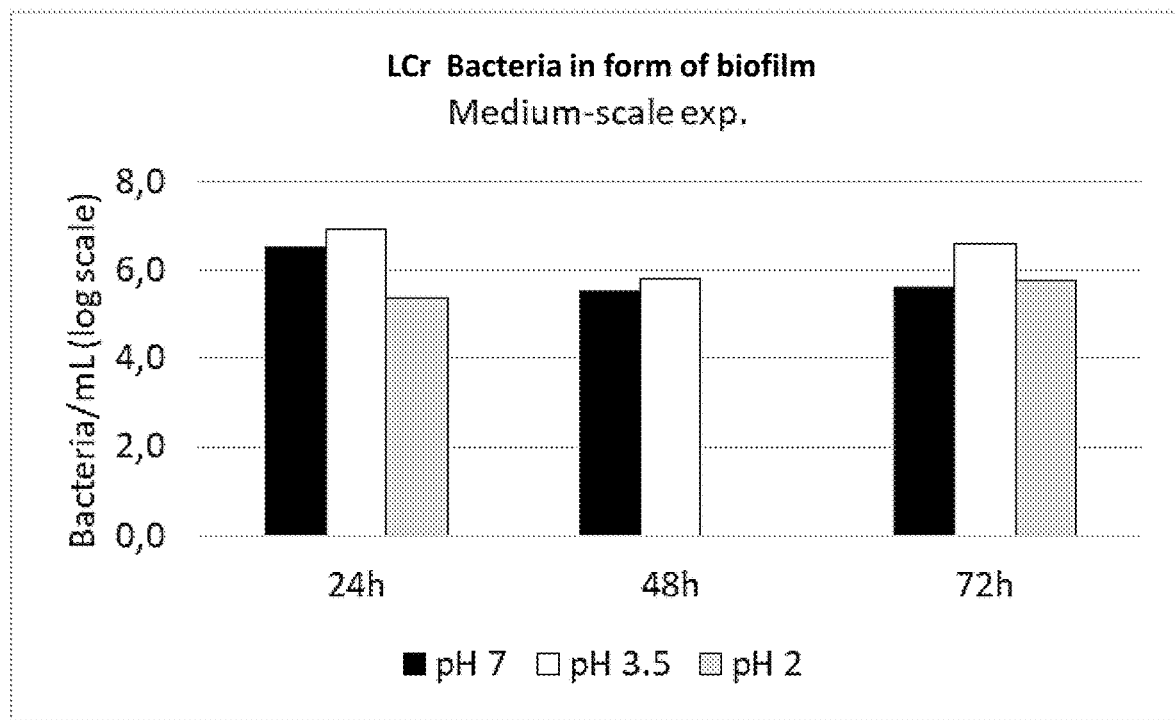
FIG. 12 presents a bar graph of acid resistance of *L. crispatus* Bacteria in form of biofilm following growth in a medium-scale set-up.

Bacteria yield in biofilm was slightly higher (~1-2 log) at the medium-scale experiment compare with the small-scale experiment (FIG. 12). However, the increase in Bacteria in form of biofilm when exposure to pH 3.5 was comparable to the ones observed in the small-scale experimental set up. High survival of LCr Bacteria in form of biofilm was recorded after the Pt and 3rd of incubation, when exposed to the lowest pH treatment. In both experimental set-up, Bacteria in form of biofilm at this pH treatment, perished after 48 h.

Figure 13:
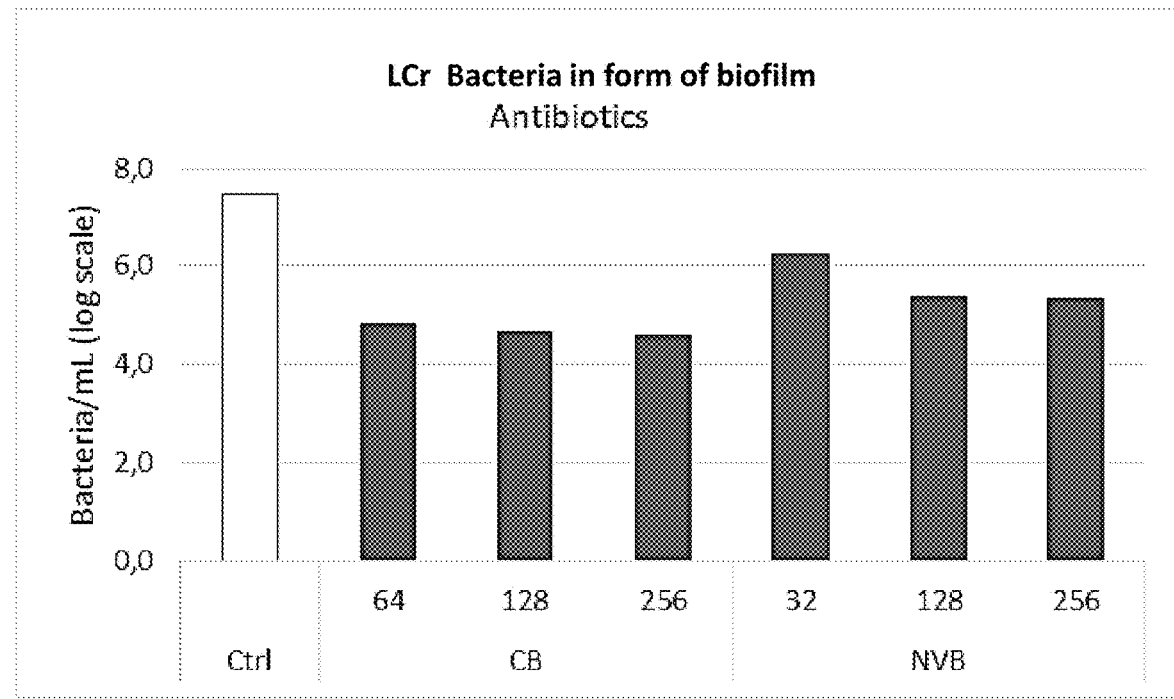
FIG. 13 presents a bar graph of antibiotics resistance of *L. crispatus* Bacteria in form of biofilm following growth in a medium-scale set-up. 'Ctrl' refers to Bacteria in form of biofilm that was not exposed to antibiotics. Numbers in the x-axis are antibiotics concertation in μg/mL.

Resistance of LCr Bacteria in form of biofilm to antibiotics was then investigated (FIG. 13). Similar to LJ Bacteria in form of biofilm, LCr Bacteria in form of biofilm showed high resistance to CB and NVB with a slightly better growth (1 log) of LCr Bacteria in form of biofilm after exposure to NOVO.

To summarize, LCr Bacteria in form of biofilm showed moderate advantage to low pH treatment over their planktonic counterpart and high advantage when tested against antibiotics. Moreover, number of biofilm cells after 24 h and 72 h of incubation and following exposure to low pH treatments were comparable.

*L. gasseri* (LG)

Planktonic LG

Figure 14:
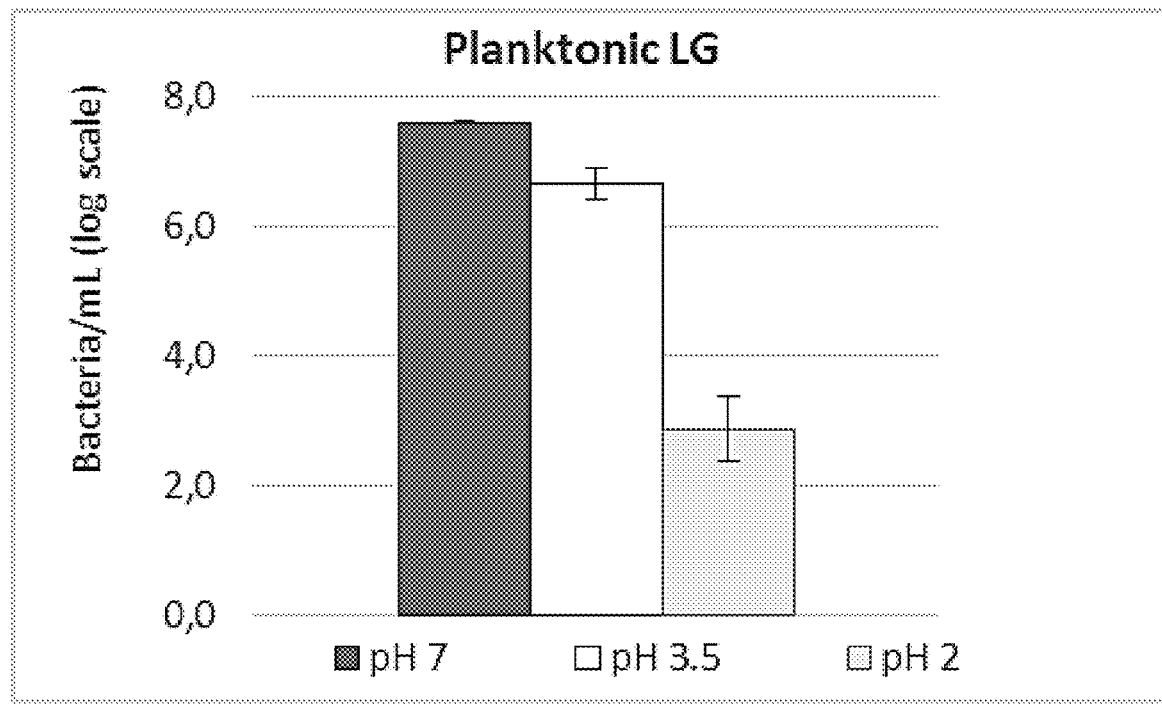
FIG. 14 presents a bar graph of acid resistance of planktonic bacteria of *L. gasseri*.

Results of planktonic LG, when exposed to acidic pH, differed from planktonic LI, LJ and LCr (FIG. 14). While exposure to pH 3.5 slightly decrease number of planktonic LG, incubation in pH 2 resulted in survival of bacteria in very low numbers.

When planktonic LG were later tested for their susceptibility to antibiotics (Table 6)), MIC values were established; similar to LJ and LCr, planktonic LG were highly sensitive to for CB, NVB and VAN (4 µg/mL, 2 µg/mL and 1.5 µg/mL, respectively) while for CIP bacteria showed full resistance.

TABLE 6

MIC of different antibiotics for planktonic LG Values are expressed in µg/mL.

| Bacteria\ABX | CB | NVB | VAN | CIP |
|---|---|---|---|---|
| Lactobacillus gasseri | 4 | 2 | 1.5 | >256 |

LG Bacteria in Form of Biofilm—Small-Scale Experiment

Figure 15:
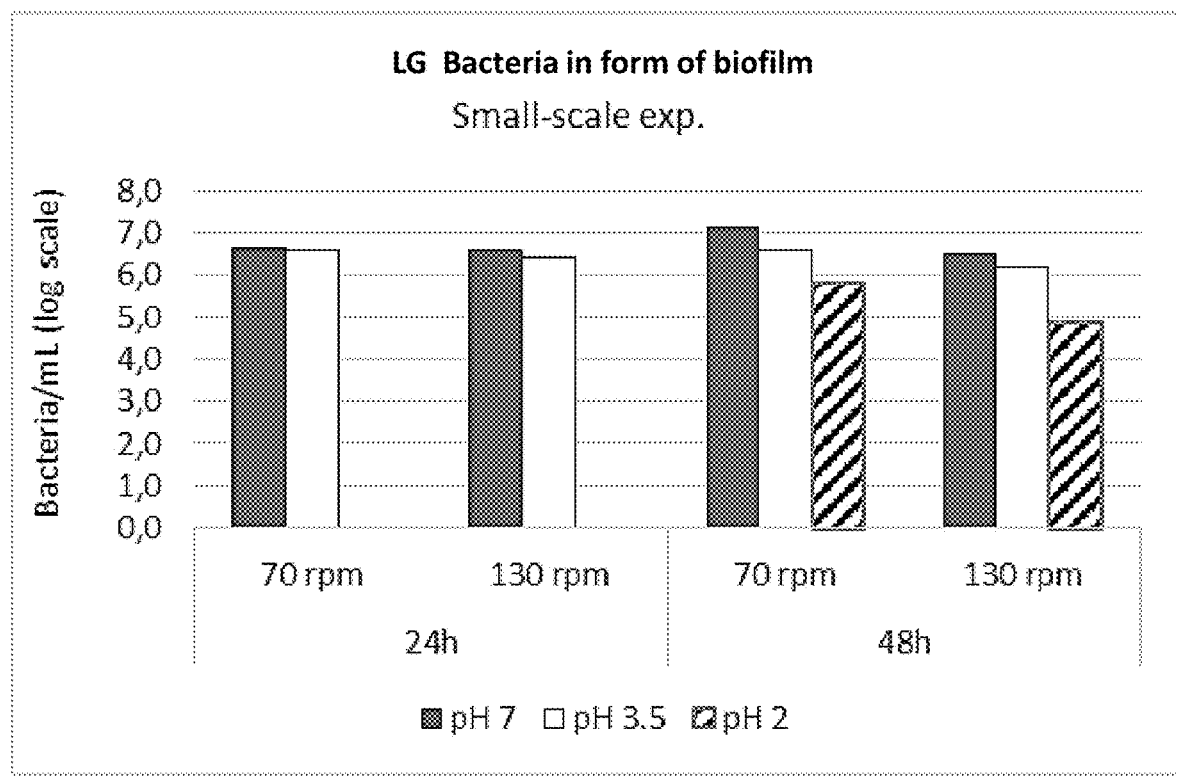
FIG. 15 presents a bar graph of acid resistance of *L. gasseri* Bacteria in form of biofilm following growth in a small-scale set-up while examining two agitation speeds (70 and 130 rpm)

Similar to LCr and LJ Bacteria in form of biofilm, no significant difference was observed between the two stirring speeds that were tested (FIG. 15). The highest bacteria yield was $10^7$ cells/mL. At 48 h, after exposure to acidic pH Bacteria in form of biofilm displayed high viability; Number of bacteria in biofilm did not differ between pH 3.5 to control whereas there was only a 1.3 and 1.6 log drop, at 70 rpm and 130 rpm respectively, in bacteria when inoculated in pH 2. This result indicates the performance of biofilm cells to be superior to that of planktonic cells, where in the latter cells completely perished at pH 2.

LG Bacteria in Form of Biofilm—Medium-Scale Experiment

Figure 16:
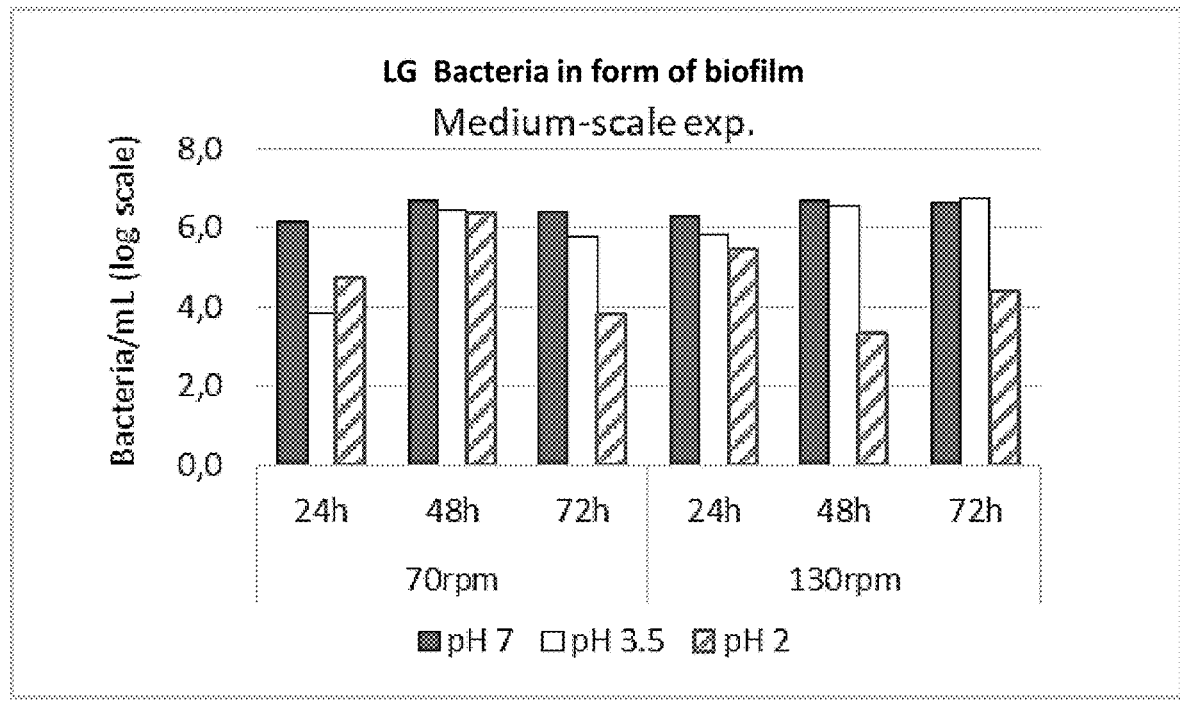
FIG. 16 presents a bar graph of acid resistance of *L. gasseri* Bacteria in form of biofilm following growth in a medium-scale set-up.

When the two agitation conditions where compared, no significant difference was detected in the number of biofilm-embedded bacteria cells (FIG. 16), regardless the incubation time. Furthermore, at both treatments, high survival of biofilm cells was observed, after exposure to the lowest pH treatment. The decrease in cells viability at this pH treatment was not more than 3.2 log (after 48 h of incubation at 130 rpm). The relatively large survival at pH 2, was observed also in other experiments (see FIGS. 22-24). At pH 3.5, survival of LG Bacteria in form of biofilm appears to be slightly better when grown at 130 rpm compared to 70 rpm. However, at pH 2, no difference was detected in the survival of Bacteria in form of biofilm between the two agitation speeds.

In a later experiment, when similar stirring speeds were tested again, growth rate of LG Bacteria in form of biofilm were more enhanced at the lower speed (results are not shown). Thus, as for the former strains in this project, the mixing speed was chosen to be 70-80 rpm for the future experiments.

Figure 17:
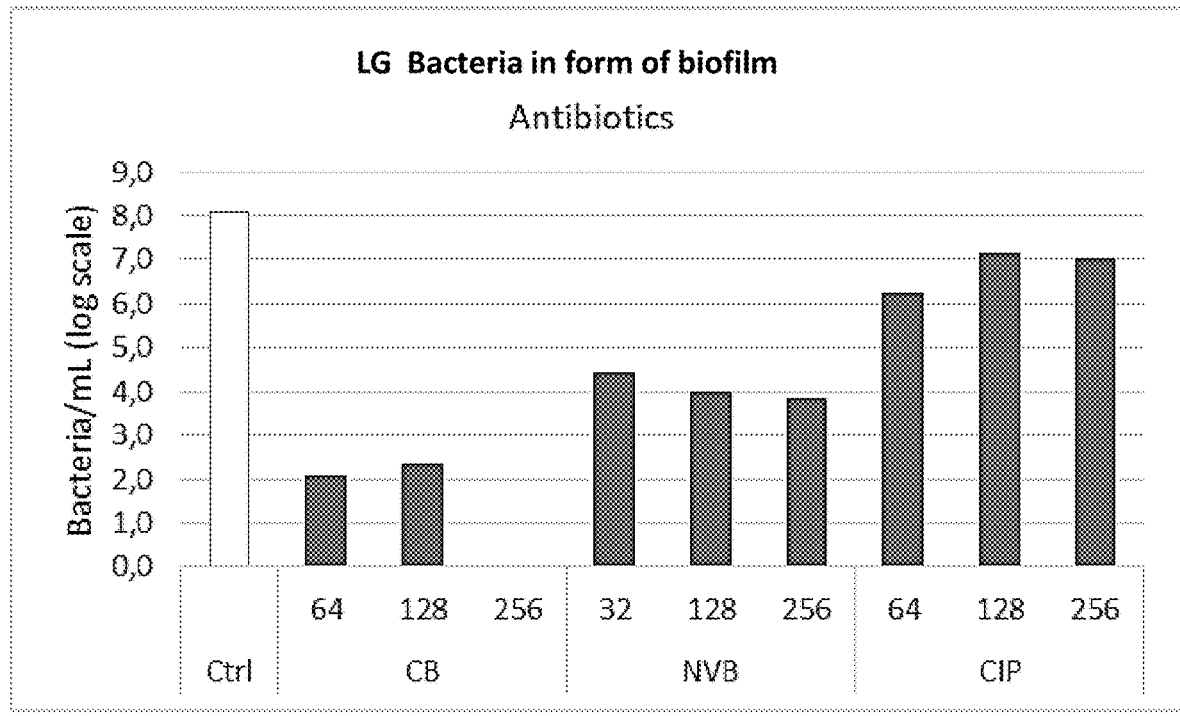
FIG. 17 presents a bar graph of antibiotics resistance of *L. iners* Bacteria in form of biofilm following growth in a medium-scale set-up. 'Ctrl' refers to Bacteria in form of biofilm that was not exposed to antibiotics. Numbers in the x-axis are antibiotics concertation in μg/mL.

LG Bacteria in form of biofilm were able to survive and grow well in the presence of NVB antibiotic (FIG. 17). However, in the presence of CB, Bacteria in form of biofilm survival was less distinct with only few colonies that grow after exposure to this antibiotic. The number of survived colonies where below the threshold that was consider as significant (FIG. 17 Dashed line).

To conclude, LG planktonic and Bacteria in form of biofilm cultures showed large difference between the two modes of growth in relation to their resistance to extreme conditions. The advantage of LG Bacteria in form of biofilm over suspended bacteria is therefore evident.

*L. rhamnosus* (LRh)

Planktonic LRh

Figure 18:
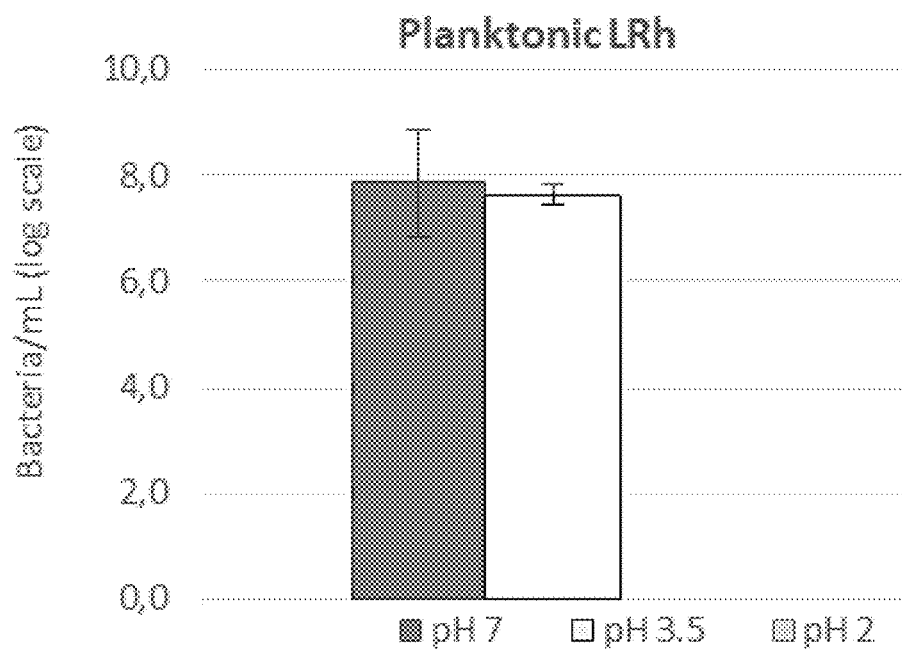
FIG. 18 presents a bar graph of acid resistance of planktonic bacteria of *L. rhamnosus*.

Planktonic LRh cells showed similar response to all bacteria strains that are described in this project, when exposed to increase acidity; no difference was detected between the control sample and Bacteria in form of biofilm exposed to pH 3.5 whereas cells disappeared at pH 2 (FIG. 18).

Similar response to the other *lactobacillus* sp. used in this project was also observed when suspended cells of LRh were exposed to CB and NVB antibiotics (MIC values of 4 and 2 µg/mL; Table 7). Nonetheless, when inoculated in the presence of CIP and VAN antibiotics, their response was opposite to the other bacteria strains; planktonic LRh were highly sensitive to CIP (0.25 µg/mL) and completely resistant to VAN (>256 µg/mL).

TABLE 7

MIC of different antibiotics for planktonic LRh Values are expressed in ug/mL.

| Bacteria\ABX | CB | NVB | VAN | CIP |
|---|---|---|---|---|
| Lactobacillus rhamnosus | 4 | 2 | >256 | 2 |

LRh Bacteria in Form of Biofilm—Small-Scale Experiment

Figure 19:
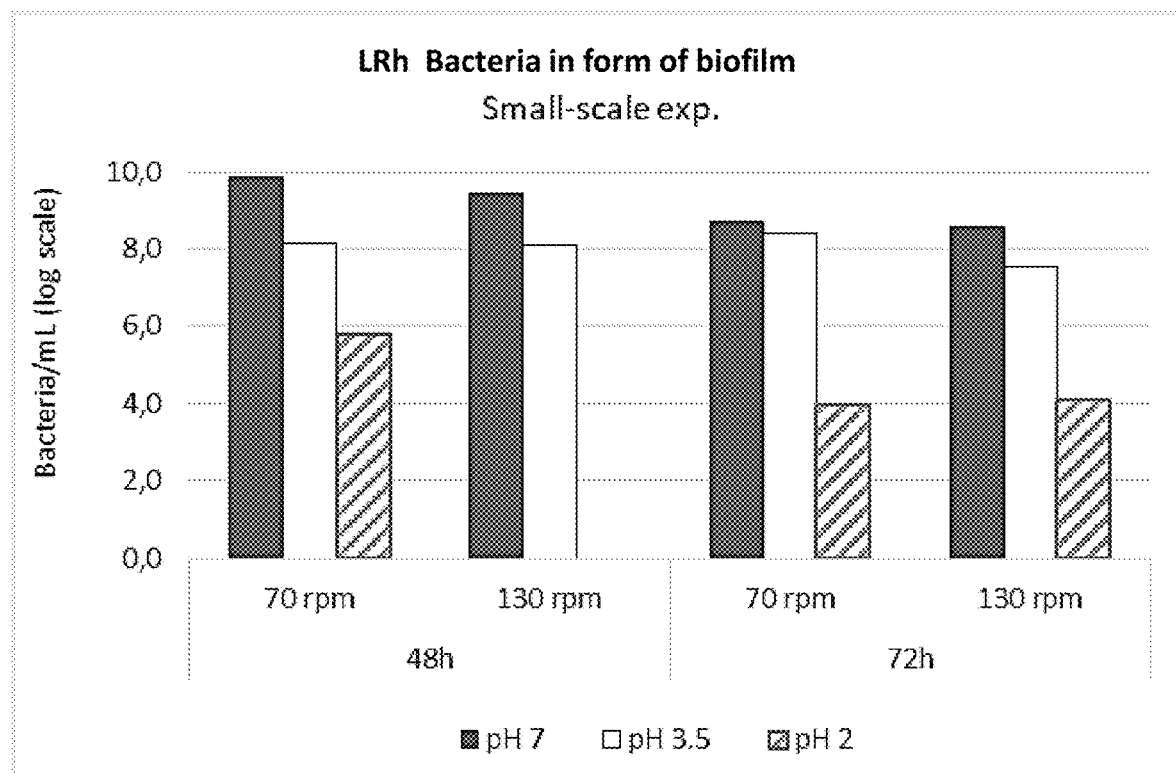
FIG. 19 presents a bar graph of acid resistance of *L. rhamnosus* Bacteria in form of biofilm following growth in a small-scale set-up while examining two agitation speeds (70 and 130 rpm)

Maximum number of biofilm-embedded bacteria was $\sim 10^{10}$ CFU/mL (FIG. 19). Overall, growth of LRh Bacteria in form of biofilm that have experienced 70 rpm seem to be slightly better than Bacteria in form of biofilm that have experienced 130 rpm; this was expressed in their high survival at pH 2 after 48 h (5.8 log) and their slightly improved survival at pH 3.5 (compare to pH 7) at the 3rd day of incubation. In addition, at 72 h of incubation there is a small decrease in the number of biofilm-embedded bacteria (Figure pH 7).

Based on the results from this experiment, the employed agitation in the next experiments was ~70-80 rpm.

LRh Bacteria in Form of Biofilm—Medium-Scale Experiment

Figure 20:
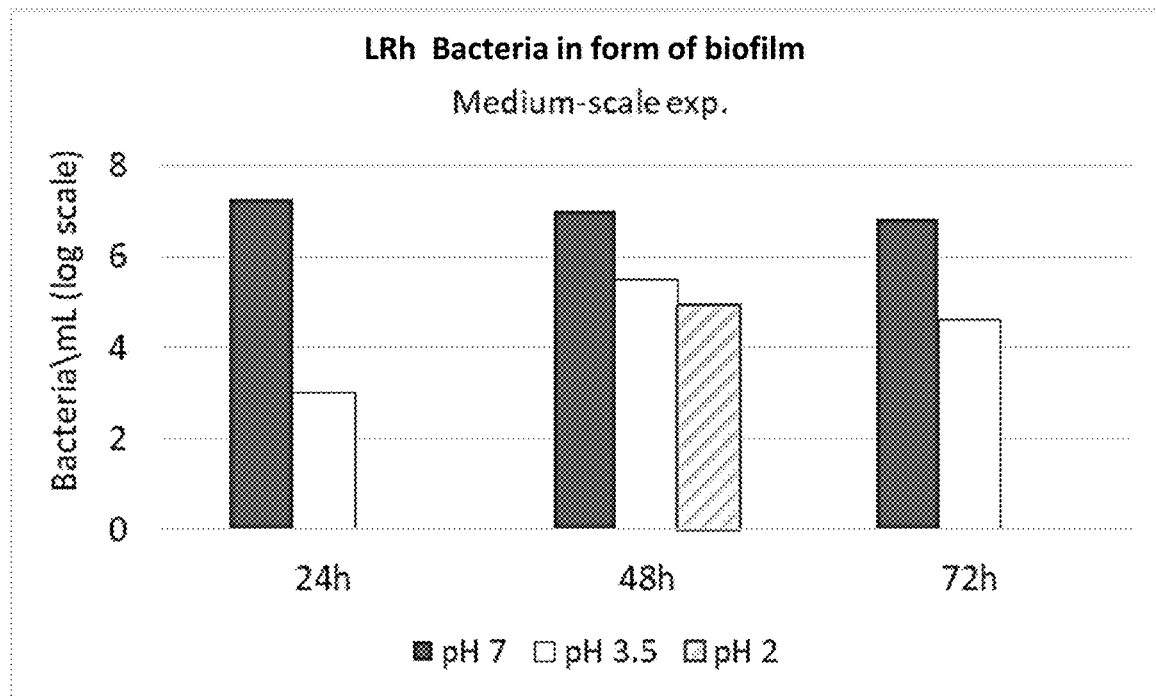
FIG. 20 presents a bar graph of acid resistance of *L. rhamnosus* Bacteria in form of biofilm following growth in a medium-scale set-up.

Unlike the former small-scale experiment, the average number of biofilm-embedded bacteria did not exceed $10^7$ CFU/mL (FIG. 20). This difference was due to an additional washing step that was included in the protocol to improve separation of the suspended bacteria from the Bacteria in form of biofilm. This washing step was then employed in all experimental designs from this point onwards. Over time, growth rate of LRh Bacteria in form of biofilm remained constant. However, in this experiment, LRh Bacteria in form of biofilm appear to better resist low pH treatments at the end of the second day of incubation; a reduction of not more than 2 logs was observed at pH 2.

Figure 21:
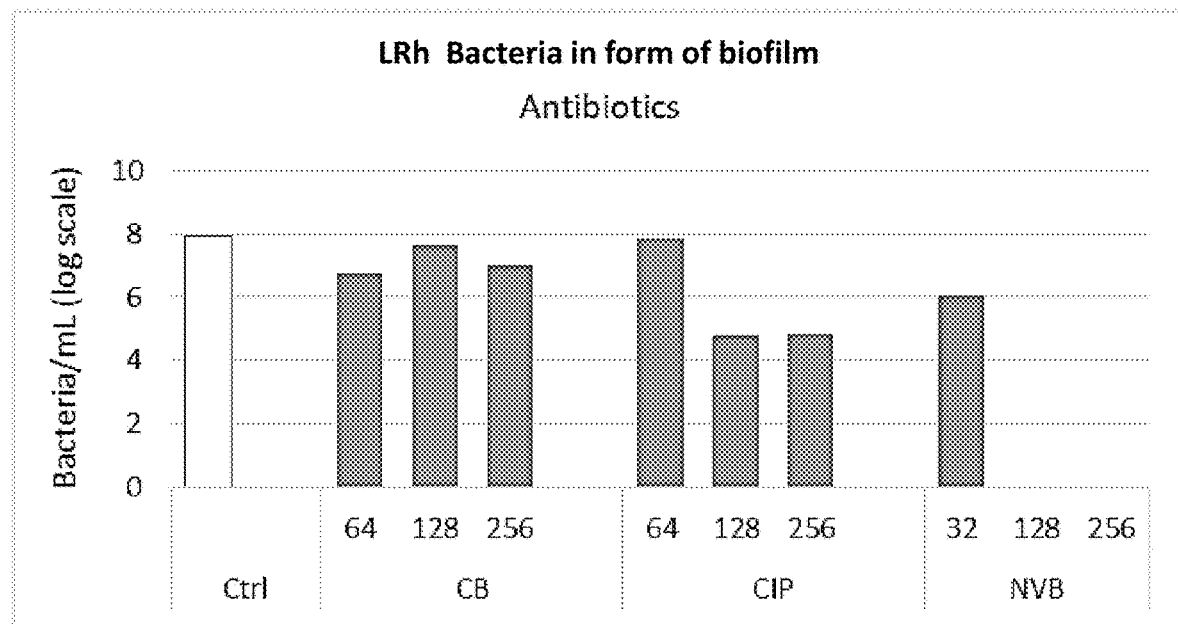
FIG. 21 presents a bar graph of antibiotics resistance of *L. rhamnosus* Bacteria in form of biofilm following growth in a medium-scale set-up. 'Ctrl' refers to Bacteria in form of biofilm that was not exposed to antibiotics. Numbers in the x-axis are antibiotics concertation in µg/mL.

In the presence of antibiotics, LRh Bacteria in form of biofilm survived and grew well when exposed to CB and CIP but did not survived the high concentrations of NVB (128 and 256 µg/mL; MIC, 2 µg/mL FIG. 21).

LRh Bacteria in form of biofilm have showed increased survived and growth in the presence of CB and CIP antibiotics, in concentrations where suspended planktonic counterparts completely disappeared.

Example 3

Evaluation of Suppositories Formulations

The formulation of the suppositories consists of Bacteria in form of biofilm, mixed in pharmaceutically acceptable excipients (oil-based carriers) and/or a supplement. Bacteria in form of biofilm was used either as lyophilized (dry) powder or as wet Bacteria in form of biofilm (at the end of 72 h incubation). A stability assay of the Bacteria in form of biofilm survival in suppositories was preformed once a month, for the duration of 6 months. Each month, one suppository from each formulation was melted in PBS(×1) and bacteria were plated for CFU counting (see Analytical methods).

Improving Active Ingredients Mixture

Additives.

High vaginal pH is associated with an increase of vaginal pathogens and the acidity of the vagina has long been understood to be a protective mechanism against colonization of anaerobes pathogens while creating a favourable environment for the lactobacilli to thrive. Examining the effect of different additives (cranberries and ascorbic acid) on Bacteria in form of biofilm LP (as part of a small scale). Here, we examined two acidifying agents, cranberries and ascorbic acid, where the former is also suggested to have a role in preventing and/or reducing recurrent of UTI infection. The aim is to add one of these additives along with the Bacteria in form of biofilm in the suppository composition. As such, their effect on Bacteria in form of biofilm survival and growth was tested. Following exposure of LP Bacteria in form of biofilm to cranberries powder (300 mg), no significant effect on Bacteria in form of biofilm survival and/or growth was recorded (FIG. 27).

Figure 22:
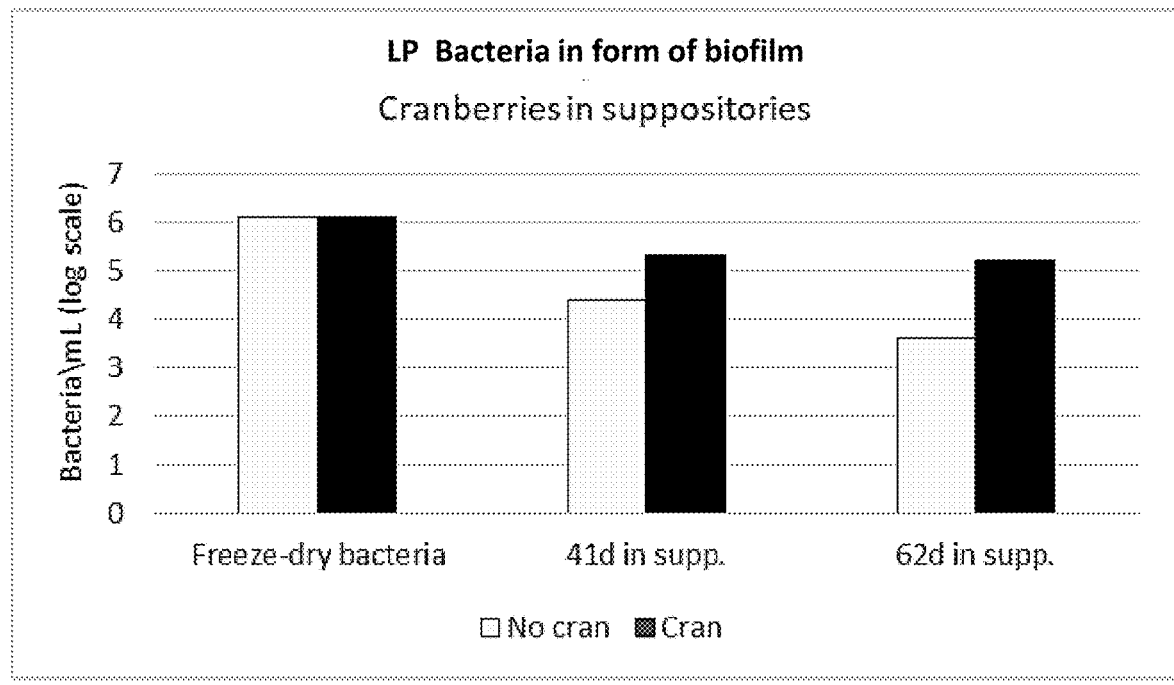
FIG. 22 presents a bar graph of the effect of cranberries on Bacteria in form of biofilm survival in suppositories during two months. 'cran' refers to cranberries; 'supp' refers to suppositories.

Interestingly, when cranberries powder was included in suppositories together with lyophilized Bacteria in form of biofilm, an enhancement in bacterial survival was observed compared to when cranberries were omitted from the suppositories (between 1 to 1.6 log higher; FIG. 22). In addition, samples were stable during two months in suppositories (FIG. 22). The addition of AA to suppositories, produced similar results to the addition of cranberries; Only a small reduction of 1 to 2 log was observed in Bacteria in form of biofilm growth. As expected, both Ascorbic Acid (AA, vitamin C) and cranberries reduced initial pH values in the MRS solution to 3.5-4. Because the addition of AA provided a more homogeneous mixture for the suppositories, it was decided to use it in later experiments.

Bacteria in Form of Biofilm.

Figure 23:
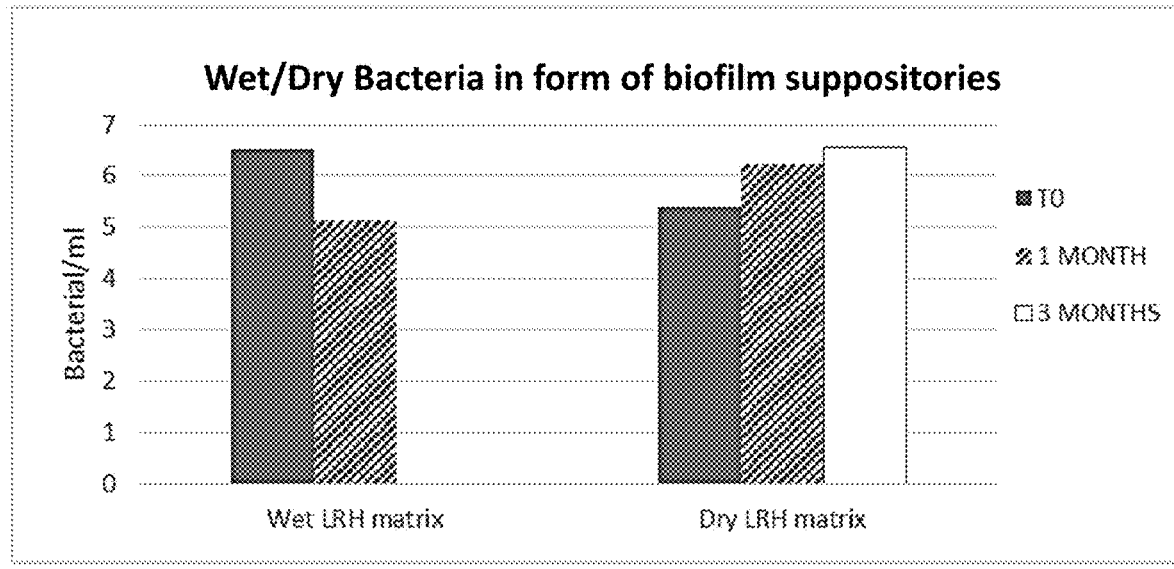
FIG. 23 presents a bar graph of survival of wet- and dry-Bacteria in form of biofilm after 1 and 3 months in suppositories.

The survival of wet Bacteria in form of biofilm (after 72 h incubation) and dry Bacteria in form of biofilm in suppositories was investigated. Results revealed that after 1 month in suppositories CFU counts of dry Bacteria in form of biofilm did not differ significantly from their number at T0 (less than 1 log). However, there was a reduction of 1.5 log in wet Bacteria in form of biofilm survival. After 3 months, however, wet Bacteria in form of biofilm of LRh completely perished while CFU count of dry Bacteria in form of biofilm in suppository remained stable. This result clearly demonstrate that humidity negatively affected Bacteria in form of biofilm survival in suppositories, and therefore the use of dry Bacteria in form of biofilm powder is essential (FIG. 23).

Improving Suppositories Excipients Mixture

Figure 24:
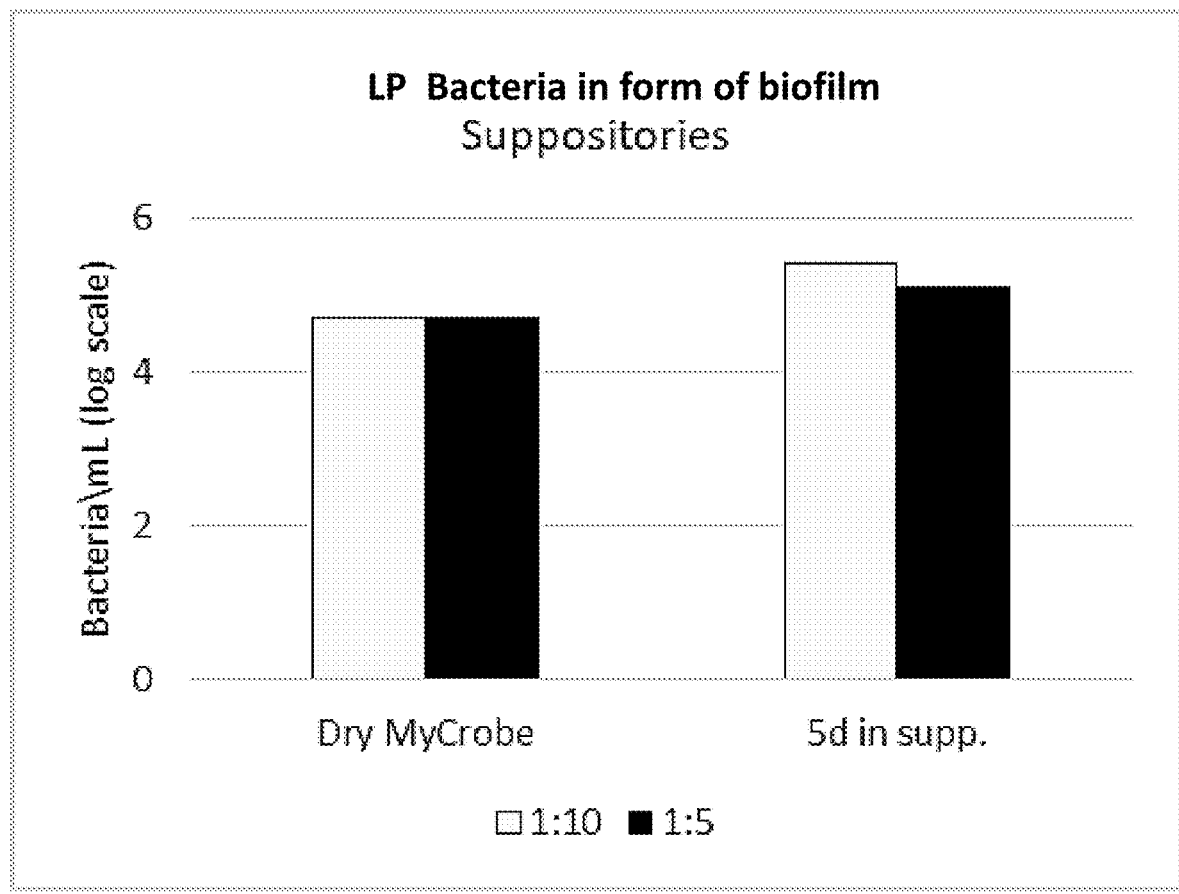
FIG. 24 presents a bar graph of survival of LP Bacteria in form of biofilm in suppositories containing different ratio of Bacteria in form of biofilm: excipients, 1:5 or 1:10, respectively. Excipients comprised of two oil-based carriers, vegetable butter and cocoa butter. 'supp' refers to suppositories.
Figure 25:
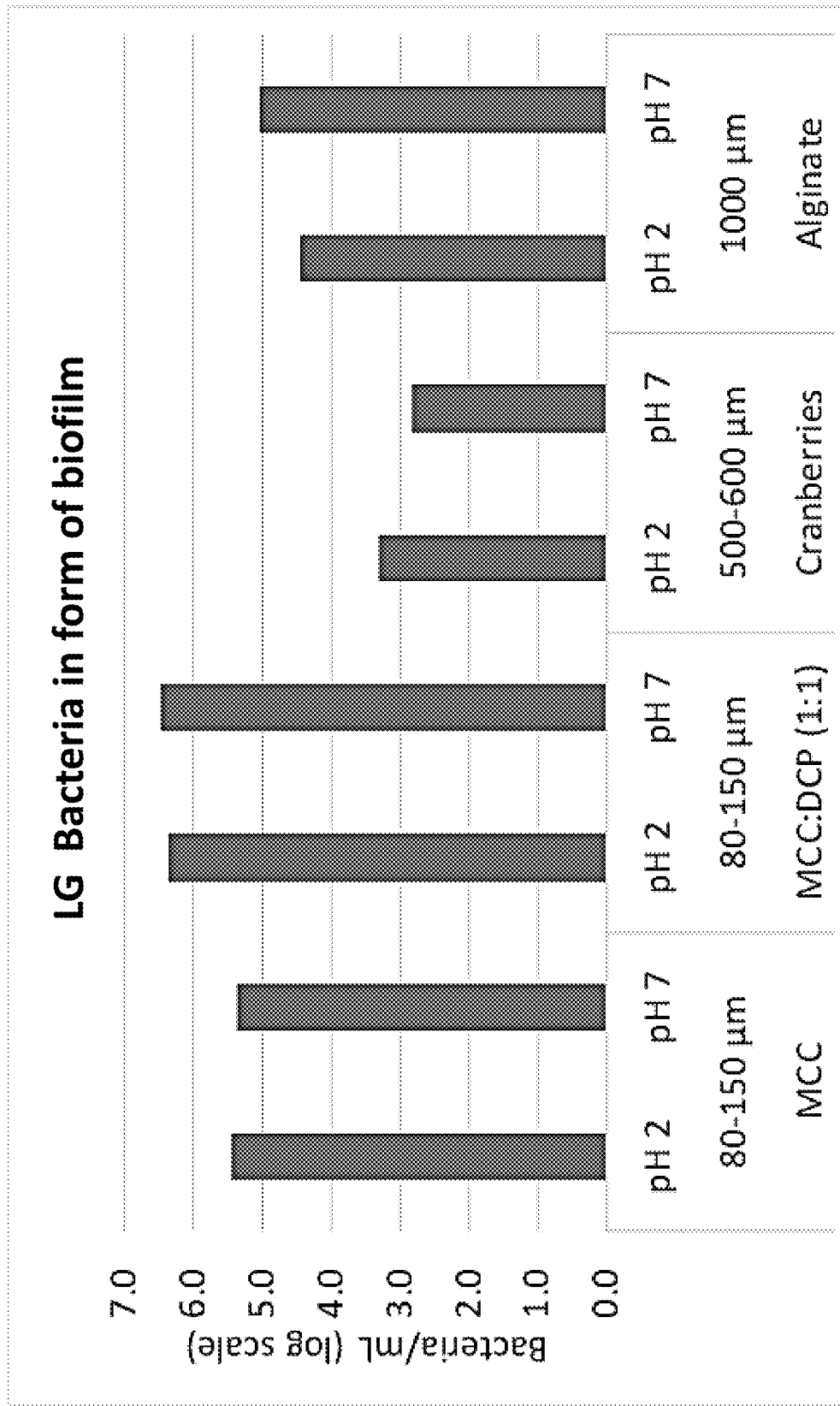
FIG. 25 presents a bar graph of the effect of different particles on the growth of LG Bacteria in form of biofilm.

After few small experiments, the basic formulation of the oil-based carriers included vegetable (palm) butter and cocoa butter, in a ratio of 1:5, respectively as well as few drops of Lecithin to aid with the homogeneity of the mixture. Next, we aimed to reduce the volume of oil-based carriers compare to Bacteria in form of biofilm, thus increasing the quantity of Bacteria in form of biofilm in the suppositories. Two ratios of Bacteria in form of biofilm to carriers were tested, 1:5 and 1:10, respectively (FIG. 24). Results showed no difference in Bacteria in form of biofilm growth between the two ratios, thus allowing us to raise Bacteria in form of biofilm quantity in the suppositories composition.

The addition of a supplement such as cranberries or vitamin C did not affect Bacteria in form of biofilm growth and their administration together with Bacteria in form of biofilm can be more effective for treating BV than the administration of each one alone.

Particle Sizes and Bacteria in Form of Biofilm Affinity to the Particles

After 24 h incubation of LG planktonic cells with different particles, LG Bacteria in form of biofilm growth and development was as follows Microcrystalline cellulose: Di calcium phosphate (MCC:DCP)>MCC>Alginate>Cranberries. Based on these results the inventors suggest that the combination of both reduced particle size and the type of matrix positively influenced LG Bacteria in form of biofilm growth and development: 1) particle sizes—smaller-particles size (higher surface to volume ratio) may allow more bacteria to attach per particle volume, thus improving Bacteria in form of biofilm growth: Bacteria in form of biofilm growth was enhanced on MCC or MCC:DCP combination (80-150 µm) compare to alginate beads (1000 µm); 2) type of matrix—the inventors suggest here two possible explanation, without wishing to be bound to any particular theory, for the contribution of the specific matrix to biofilm growth and formation. Despite alginate being twice as big as cranberries, LG Bacteria in form of biofilm growth was higher when inoculated with alginate. One assumption is the lower pH that is induced by the presence of cranberries in the solution, which might negatively have affected Bacteria in form of biofilm growth. Another speculation is based to the fact that alginate is one of bacterial polysaccharides that was shown to be important for biofilm formation. Another example is the difference in the number of LG biofilms cells between MCC to MCC:DCP. Few studies have shown that exogenous Calcium ions can promote biofilm formation, hence the presence of soluble DCP particles (dicalcium phosphate) and subsequently calcium ions may enhance growth and development of LG biofilm.

Example 4

Suppositories Formulations

A new combination of bacteria with Pentasa (anti-inflammatory agent) as rectal/vaginal suppositories, is shown.

Two formulations were compared, a formulation A with dry Bacteria in form of biofilm, and a formulation B, with a combination of Pentasa and Bacteria in form of biofilm (Table 8).

TABLE 8

|   | Amount  | Oil/fatty | Dry Bacteria              | Medicine    |
|---|---------|----------|---------------------------|-------------|
| A | 3 units | 8 g      | LCr, LJ, LG, LGG 0.5 g each | —           |
| B | 3 units | 8 g      | LGG, LG 0.66 g each       | Pentasa 0.66 g |

Figure 26:
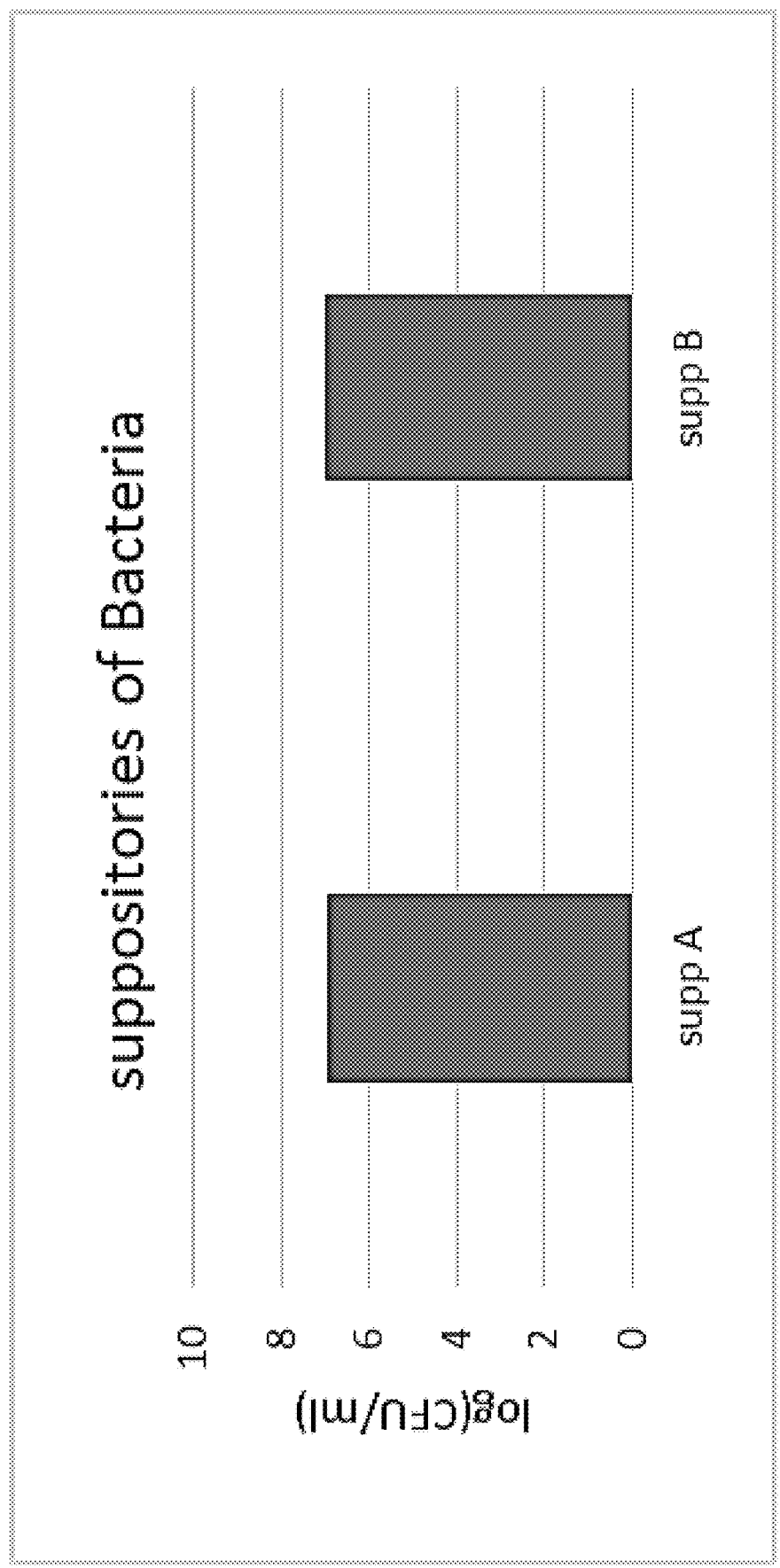
FIG. 26 presents a bar graph comparing the stability of a suppository formulation comprising a combination of Pentasa with Bacteria in form of biofilm.

When tested the combination of Pentasa with dry Bacteria in the form of biofilm, the stability of the bacteria maintained (FIG. 26). The same was observed for planktonic bacteria with Pentasa.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition in the form of a suppository, comprising:
   (i) at least one viable probiotic bacteria in the form of dried biofilm;
   (ii) a first agent comprising an antibiotic agent;
   (iii) a first lipophilic carrier; and
   optionally (iv) a pH adjusting agent,
      wherein said at least one probiotic bacteria is 10% to 50% (w/w) of the total composition, and
      wherein said at least one probiotic bacteria and said antibiotic agent are homogeneously dispersed within said first lipophilic carrier.

2. The composition of claim 1, further comprising a second layer.

3. The composition of claim 2, wherein said second layer comprises a second lipophilic carrier, a second agent or both.

4. The composition of claim 3, wherein said first lipophilic carrier and said second lipophilic carrier have each independently a characteristic selected from (i) a melting point in the range of 25° C. to 60° C. (ii) comprising one or more hydrogenated fats.

5. The composition of claim 3, wherein any one of: (i) said second lipophilic carrier has a melting point at least 5° C. higher than said first lipophilic carrier; and (ii) said first lipophilic carrier has a melting point at least 5° C. higher than said second lipophilic carrier.

6. The composition of claim 3, wherein the release of said at least one probiotic bacteria in the form of biofilm is slower than the release of said second agent.

7. The composition of claim 3, wherein said first lipophilic carrier and said second lipophilic carrier comprise cacao butter, palm oil, plant wax, vegetable wax, or any combination thereof.

8. The composition of claim 1, wherein the biofilm is attached to a particle in the range of 50 micrometers to 1500 micrometers (μm).

9. The composition of claim 1, wherein said at least one probiotic bacteria is selected from the genera *Lactobacillus, Bifidobacterium, Saccharomyces, Streptococcus, Faecalibacterium*, and any combination thereof.

10. The composition of claim 3, wherein said second agent is an antibiotic.

11. The composition of claim 1, wherein said first agent and pH adjusting agent selected from the group consisting of: sodium bicarbonate, ascorbic acid, citric acid, acetic acid, fumaric acid, propionic acid, malic acid, succinic acid, gluconic acid, tartaric acid, lactic acid, boric acid, and cranberry extract.

12. The composition of claim 1, further comprising a stabilizer, a preservative, a lubricant, a viscosity modifying agent, a buffering agent, a fatty acid, and combinations thereof.

13. A method for restoring the native vaginal or gut flora and/or treating or reducing the risk of urogenital infections, dysbiosis, ulcerative colitis, inflammatory bowel disease (IBD), Crohn's disease, or any combination thereof, in a subject, comprising administering an effective amount of the composition of claim 1 to said subject.

14. The method of claim 13, wherein the release of said at least one probiotic bacteria is controlled by said lipophilic carrier.

* * * * *